United States Patent [19]
Brennan

[11] Patent Number: 6,130,074
[45] Date of Patent: *Oct. 10, 2000

[54] RECOMBINANT INSECT VIRUS WITH REDUCED CAPACITY FOR HOST-TO-HOST TRANSMISSION IN THE ENVIRONMENT AND METHODS TO PRODUCE SAID VIRUS

[75] Inventor: Lynn Ann Brennan, Hopewell, N.J.

[73] Assignee: American Cyanamid Company Five Giralda Farms, Madison, N.J.

[ * ] Notice: This patent is subject to a terminal disclaimer.

[21] Appl. No.: 08/069,044

[22] Filed: May 28, 1993

Related U.S. Application Data

[63] Continuation-in-part of application No. 08/057,717, May 4, 1993, abandoned, which is a continuation of application No. 07/891,598, Jun. 1, 1992, abandoned.

[51] Int. Cl.[7] ............................ C12N 15/63; C12N 15/64; C12N 15/866; C12N 5/10
[52] U.S. Cl. ...................................... 435/91.41; 435/235.1; 435/320.1; 435/325; 435/348; 435/91.42; 435/91.4
[58] Field of Search .............................. 435/235.1, 320.1, 435/69.1, 172.1, 172.3, 325, 348, 91.4, 91.41, 91.42

[56] References Cited

FOREIGN PATENT DOCUMENTS

| 54780/90 | 11/1990 | Australia . |
|---|---|---|
| 8802030 | 3/1988 | WIPO . |
| WO 92/14818 | 9/1992 | WIPO . |
| WO 93/03144 | 2/1993 | WIPO . |
| WO 93/25666 | 12/1993 | WIPO . |

OTHER PUBLICATIONS

Hashimoto et al., J. gen. Virol., vol. 77, pp. 555–563, 1996.
Tanada et al. In "Atlas of Invertebrate Viruses", Eds. Jean R Adams and Jean R. Bonami, CRC Press, Boca Raton, 1991.
Werstuck et al. "Enhanced Infectivity of Herpes Simplex Virus Type 1 Viral DNA in a Cell Line Expressing the trans–Inducing Factor Vmw 65" Journal of Virology, Mar. 1990, vol. 64, No. 3, pp. 984–991.
Hamblin, M., et al., App. & Envir. Microbiology, 56, 3057–3062 (1990).
Gonzalez, M. A., et al., Virology, 170, 160–175 (1989).
Wood, H. A., et al., Ann. Rev. Microbiol., 45, 69–87 (1991).
Rohrman, G. F., J. gen. Virol., 67, 1499–1513 (1986).
Winstanley, D., et al., J. gen. Virol., 74, 1599–1609 (1993).
Burand, J., et al., Sequence Analysis of the Gypsy Moth Virus Virulence Gene, p77, Proceedings U.S. Department of Agriculture Interagency Gypsy Moth Research Forum 1992, Annapolis, MD (Jan. 13–16, 1992).
Hill, J. E., et al., Biochim. et Biophys. Acta, 1172, 187–189 (1993).

*Primary Examiner*—David Guzo
*Attorney, Agent, or Firm*—Darryl L. Webster; Alan M. Gordon

[57] ABSTRACT

A noninfectious insect virus is described having an altered genetic element whose function is restored by genetic complementation, thereby again producing the insect infectious form of the virus. Also described is the insertion of a heterologous gene into the viral genome, such that an insect controlling or modifying substance is also produced by the virus for an improved bioinsecticidal effect and genetic stability of desired traits.

89 Claims, 4 Drawing Sheets

RECOMBINANT INSECT VIRUS WITH REDUCED CAPACITY FOR HOST-TO-HOST TRANSMISSION IN THE ENVIRONMENT AND METHODS TO PRODUCE SAID VIRUS

This application is a continuation-in-part of U.S. Ser. No. 08/057,717, filed May 4, 1993, now abandoned, which in turn is a continuation of U.S. Ser. No. 07/891,598, filed Jun. 1, 1992, now abandoned, which are both incorporated herein by reference in their entirety.

FIELD OF THE INVENTION

This invention relates to a noninfectious insect virus having an altered genetic element whose function is restored by genetic complementation, thereby again producing the insect infectious form of the virus. This invention further relates to the insertion of a heterologous gene into the viral genome, such that an insect controlling or modifying substance is also produced by the virus for an improved bioinsecticidal effect and genetic stability of desired traits.

BACKGROUND OF THE INVENTION

The following abbreviations are used throughout this application:
A. cal.—Autographa californica
AcMNPV—Autographa californica nuclear polyhedrosis virus
bp—base pairs
ECV—extracellular virus
GV—granulosis virus
kD—kilodaltons
MOI—multiplicity of infection
NPV—nuclear polyhedrosis virus
OB—occlusion body
OV—occluded virus
PCR—polymerase chain reaction
PDV—polyhedron derived virus
p.i.—post-infection
PIB—polyhedron inclusion body (also known as OB)
5' UTR—the mRNA or gene sequence corresponding to the region extending from the start site of gene transcription to the last base or basepair that precedes the initiation codon for protein synthesis
3' UTR—the mRNA or gene sequence corresponding to the region extending from the first base or basepair after the termination codon for protein synthesis to the last gene-encoded base at the 3' terminus of the mRNA
(+)-strand—the DNA strand of a gene and its flanking sequences which has the same sense as the RNA that is derived from that gene
(−)-strand—the DNA strand of a gene and its flanking sequences that is complementary to the (+) strand The present invention applies to all insect viruses, including DNA and RNA viruses. The DNA viruses include entomopox viruses (EPV), and Baculoviridae viruses, such as nuclear polyhedrosis viruses (NPV) and granulosis viruses (GV), and the like. The RNA viruses include togaviruses, flaviviruses, picornaviruses, cytoplasmic polyhedrosis viruses (CPV), and the like. The Subfamily of double stranded DNA viruses Eubaculovirinae includes two genera, NPVs and GVs, which are particularly useful for biological control because they produce occlusion bodies (OBs) in their life cycle.

Over 400 baculovirus isolates have been described. The Autographa californica nuclear polyhedrosis virus (AcMNPV) is the prototype virus of the Family Baculoviridae and has a wide host range. The AcMNPV virus was originally isolated from Autographa californica (A. cal.), a lepidopteran noctuid (which in its adult stage is a nocturnal moth), commonly known as the alfalfa looper. This virus infects 12 Families and more than 30 species within the order of Lepidopteran insects (Bibliography entry 1). It is not known to infect productively any species outside this order.

The use of baculoviruses as bioinsecticides holds great promise. One of the major impediments to their widespread use in agriculture is the time lag between initial infection of the insect and its death. This lag can range from a few days to several weeks. During this lag, the insect continues to feed, causing further damage to the plant. A number of researchers have attempted to overcome this drawback by inserting a heterologous gene into the viral genome, so as to express an insect controlling or modifying substance, such as a toxin (2,3,4), neuropeptide and hormone (5,6) or enzyme (7).

While genetic engineering provides a means for overcoming technical obstacles to the commercialization of viruses as bioinsecticides, it has also given rise to a perception that there may be a second potential impediment to their widespread acceptance. In particular, there is speculation that release of these genetically engineered viruses into the environment may result in unforseen consequences to the ecosystem as these viruses replicate and spread (8,9). To date, all recombinant insect viruses produced for the biocontrol of insects would be subject to this speculation because all are capable of insect to insect transmission. Thus, there is a need for recombinant insect-specific viruses which have a reduced capacity for insect to insect (host-to-host) transmission following their release into the environment.

The life cycle of baculoviruses, as exemplified by AcMNPV, includes two stages. Each stage of the life cycle is represented by a specific form of the virus: Extracellular viral particles (ECV) which are nonoccluded, and occluded virus particles (OV) (10,11). The extracellular and occluded virus forms have the same genome, but exhibit different biological properties. The maturation of each of the two forms of the virus is directed by separate sets of viral genes, some of which are unique to each form.

In its naturally occurring insect infectious form, multiple virions are found embedded in a paracrystalline protein matrix known as an occlusion body (OB), which is also referred to as a polyhedron inclusion body (PIB). The proteinaceous viral occlusions are referred to as polyhedra (polyhedron is the singular term). A polyhedrin protein, which has a molecular weight of 29 kD, is the major viral-encoded structural protein of the viral occlusions (10, 12). (Similarly, GVs produce OBs which are composed primarily of granulin, rather than polyhedrin).

The viral occlusions are an important part of the natural baculovirus life cycle, providing the means for horizontal (insect to insect) transmission among susceptible insect species. In the environment, a susceptible insect (usually in the larval stage) ingests the viral occlusions from a contaminated food source, such as a plant. The crystalline occlusions dissociate in the gut of the susceptible insects to release the infectious viral particles. These polyhedron derived viruses (PDV) invade and replicate in the cells of the midgut tissue (10).

It is believed that virus particles enter the cell by endocytosis or fusion, and the viral DNA is uncoated at the nuclear pore or in the nucleus. Viral DNA replication is detected within six hours. By 10–12 hours post-infection (p.i.), secondary infection spreads to other insect tissues by the budding of the extracellular virus (ECV) from the surface of the cell. The ECV form of the virus is responsible for cell to cell spread of the virus within an individual infected insect, as well as transmitting infection in cell culture.

Late in the infection cycle (12 hours p.i.), polyhedrin protein can be detected in infected cells. It is not until 18–24 hours p.i. that the polyhedrin protein assembles in the nucleus of the infected cell and virus particles become embedded in the proteinaceous occlusions. Viral occlusions accumulate to large numbers over 4–5 days as cells lyse. These polyhedra have no active role in the spread of infection in the larva. ECVs in the haemolymph multiply and spread, leading to the death of the larva (10,11,12).

When infected larvae die, millions of polyhedra remain in the decomposing tissue, while the ECVs are degraded. When other larvae are exposed to the polyhedra, for example, by ingestion of contaminated plants or other food material, the cycle is repeated (10).

In summary, the occluded form of the virus is responsible for the initial infection of the insect through the gut, as well as the environmental stability of the virus. PDVs are essentially not infectious when administered by injection, but are highly infectious orally. The non-occluded form of the virus (i.e., ECV) is responsible for secondary and cell to cell infection. ECVs are highly infectious for cells in culture or internal insect tissues by injection, but essentially not infectious by oral administration.

The use of recombinant baculoviruses expressing foreign proteins which are toxic to insects is facilitated by the fact that these viruses are not pathogenic to vertebrates or plants. In addition, the baculoviruses generally have a narrow host range. Many strains are limited to one or a few insect species.

The most widely studied baculovirus is AcMNPV. AcMNPV is known to infect 12 Families and more than 30 species within the insect order Lepidoptera (1). It is not known to infect productively any species outside this order. Both the general public and various regulatory agencies have discussed the potential consequences of a release of a strain of AcMNPV containing a foreign DNA sequence (8,9). This relates to the possibility that the engineered virus could spread into non-target lepidopterans. Another factor to consider is the known environmental stability of these viruses.

Thus, there is a need for recombinant insect-specific viruses with a reduced ability to spread from insect to insect (host to host). These viruses should be able to infect an insect, but should have a significant decrease in the ability to be transmitted from insect to insect, thereby limiting the persistence of the virus in the environment.

SUMMARY OF THE INVENTION

This invention provides for the construction and growth of recombinant insect viral strains which have a reduced capacity to spread from insect to insect, that is, have a reduced capacity for host-to-host transmission in the environment. The viruses of the Family Baculoviridiae are particularly amenable to the construction of such strains, because of their two stage life cycle described above.

These viral strains are obtained by first altering a genetic element so as to render the virus noninfectious to insects. For the purposes of this application, a genetic element is not limited to genes that code for trans-acting substances, such as RNA or protein molecules, but also include cis-acting elements or regulatory sequences, such as transcriptional enhancers, promoters, other transcriptional, translational and genome replication control elements, and viral DNA (or RNA) packaging sequences.

The alteration takes the form of a deletion, a frame shift, an insertion, a rearrangement, a point mutation, or other types of disruption of gene function. Other forms of alteration include methods which interfere with viral function, such as suppression of transcription or translation, use of an antisense RNA, insertion of an additional genetic element, and insertion of an additional regulatory element, such as the yeast upstream-activating sequence which requires the presence of the GAL 4 protein for activity ($UAS_{GAL}$).

The goal of restoring infectivity of the recombinant virus while significantly reducing host-to-host transmission is achieved by complementing with the product or function which is missing from or defective in the altered virus.

Various methods of producing the insect infectious form of the recombinant insect virus by genetic complementation are included within the scope of this invention, namely: (1) production in insect tissue culture cells transfected with a fragment of DNA which provides the product or function which is missing from or defective in the altered virus; (2) production in insect cell lines which have been stably transformed with a fragment of DNA which provides the product or function which is missing from or defective in the altered virus; and (3) production in transgenic insects which contain a fragment of DNA which provides the product or function which is missing from or defective in the altered virus.

Depending on the product or function which is being provided, it may be necessary or desirable to use a heterologous viral or cellular promoter to control the expression of the DNA fragment. This may be necessitated by dosage and temporal considerations.

The insect cells of methods (1) and (2) and the transgenic insects of method (3) thus function as "helpers" to restore the infectivity of the virus, such that the virus particles (virions) thus produced cause an infection when ingested by insects in nature. The virions produced in the infected larvae are defective because they are not complemented and, thus, the infection is not spread readily to other insects. Therefore, in the absence of a co-infecting wild-type virus, the life cycle of the recombinant virus ends with this single infection.

In a preferred embodiment of this invention, a gene coding for an insect controlling or modifying substance is inserted into the viral genome. The gene is inserted into the altered virus at any suitable location within the viral genome. Such substances include toxins, neuropeptides and hormones, and enzymes. A substance thus expressed enhances the bioinsecticidal effect.

In particular, the gene is inserted adjacent to or directly into the site of alteration of the genetic element responsible for the reduced ability for host to host transmission. The insertion of the heterologous gene adjacent to or at the site of alteration of the genetic element prevents or greatly minimizes genetic recombination that might generate a form of the virus having both a wild-type phenotype and an insect controlling or modifying gene for host-to-host transmission.

DETAILED DESCRIPTION OF THE INVENTION

Figure 1:
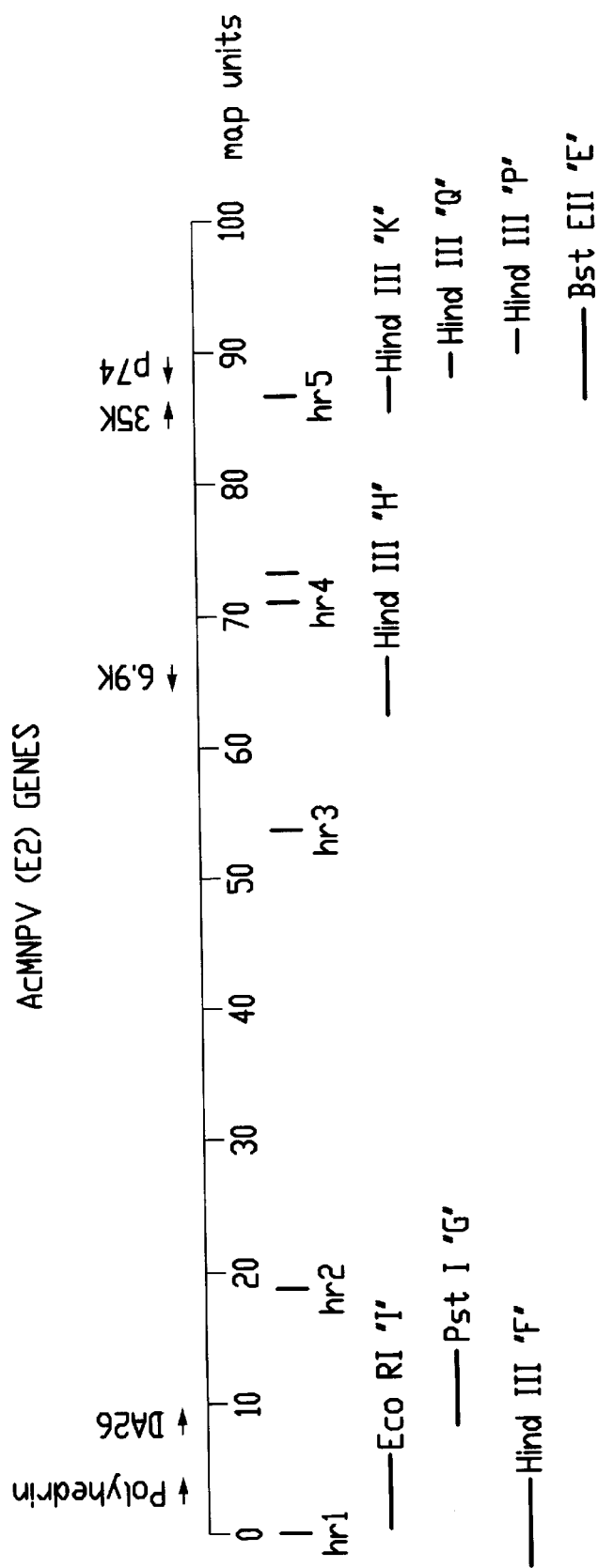
FIG. 1 depicts a linear map of known baculovirus genes of the AcMNPV genome (13).

Engineering of an insect virus with reduced spread from one insect to another results in an increased rate of loss of infectious virus from the environment beyond the rate achieved by natural processes of abiotic and biotic degradation. Hence, the engineered virus will not establish itself in the environment.

The present invention applies to all insect viruses, including DNA and RNA viruses. The DNA viruses include double stranded enveloped DNA viruses such as (Subfamily, then species) Entomopoxvirinae (*Melolontha melolontha* entomopoxvirus), Eubaculovirinae (*Autographa californica* MNPV; *Heliocoverpa zea* NPV; *Trichoplusia ni* GV), Nudibaculovirinae (*Heliocoverpa zea* NOB), Ichnovirus (*Campoletis sonorensis* virus), and Bracovirus (*Cotesia melanoscela* virus), as well as double stranded nonenveloped DNA viruses such as Iridoviridae (*Chilo iridescent* virus) and single stranded nonenveloped DNA viruses such as Parvoviridae (Galleria densovirus).

The RNA viruses include double stranded enveloped RNA viruses such as Togaviridae (Sindbis virus), Bunyaviridae (Beet leafcurl virus) and Flaviviridae (Wesselbron virus), as well as double stranded nonenveloped RNA viruses such as Reoviridae (corriparta virus) and Birnaviridae (Drosophila X virus), as well as single stranded nonenveloped RNA viruses such as Picornaviridae (Cricket paralysis virus), Tetraviridae (Nudaurelia beta virus) and Nodaviridae (Black beetle virus).

The Subfamily of double stranded DNA viruses Eubaculovirinae includes two genera, nuclear polyhedrosis viruses (NPVs) and granulosis viruses (GVs), which are particularly useful for biological control because they produce occlusion bodies in their life cycle. Examples of NPVs include *Lymantria dispar* NPV (gypsy moth NPV), *Autographa californica* MNPV, *Anagrapha falcifera* NPV (celery looper NPV), *Spodoptera littoralis* NPV, *Spodoptera frugiperda* NPV, *Heliothis armigera* NPV, *Mamestra brassicae* NPV, *Choristoneura fumiferana* NPV, *Trichoplusia ni* NPV, *Heliocoverpa zea* NPV, *Rachiplusia ou* NPV, etc. Examples of GVs include *Cydia pomonella* GV (coddling moth GV), *Pieris brassicae* GV, *Trichoplusia ni* GV, *Artogeia rapae* GV, *Plodia interpunctella* GV (Indian meal moth), etc. Examples of entomopox viruses include *Melolontha melolontha* EPV, *Amsacta moorei* EPV, *Locusta migratoria* EPV, *Melanoplus sanguinipes* EPV, *Schistocerca gregaria* EPV, *Aedes aegypti* EPV, *Chironomus luridus* EPV, etc.

Control of insects, particularly the orders Lepidoptera, Orthoptera, Diptera, Isoptera, Hymenoptera, Homoptera, Hemiptera and Coleoptera, and protection of agronomic crops, trees, shrubs, orchards and ornamentals from attack by these insects is achieved by the use of the invention of this application.

Although the invention will be exemplified for *Autographa californica* NPV (AcMPNV), it is understood that the concepts described herein are applicable for all the above-listed insect viruses. It is further contemplated that the present invention will be highly useful in improving new insect viruses which are not yet identified and classified in the literature.

Infection with AcMNPV initially results in the production of the budded form of the virus known as the ECV. The ECV is responsible for cell to cell spread of the virus within an individual infected insect, as well as during growth in cell culture. In the case of the NPVs, late in the infection cycle the cell begins producing the PDV form, which is packaged in a crystalline occlusion body (OB), which is also referred to as a polyhedron inclusion body (PIB). (Similarly, GVs produce OBs which are composed primarily of granulin, rather than polyhedrin). This PDV form of the virus is responsible for the initial infection of the insect through the gut, as well as the environmental stability of the virus.

Alteration of a function involved in production of an intact infectious OB which does not affect the budded form of the virus (ECV) is particularly useful.

Such mutations have been found in the AcMNPV (14). A number of mutagenesis experiments have identified genetic loci in which budded virus is produced, but in which intact infectious polyhedra are not produced. One of the most interesting and potentially useful loci that has been identified is the p74 gene contained in the Hind III fragment "P" of the AcMNPV genome (15). p74 is a protein produced late in baculovirus infection and at relatively low levels (15).

Homologs for the p74 gene have been identified in other NPVs, including *Choristoneura fumeiferana* NPV (16) and *Orgyia pseudotsugata* NPV (17). A homolog for p74 should be present in all members of the genus Nuclear Polyhedrosis Virus. Similarities between the life cycles of the NPVs and related genus Granulosis Viruses make it highly probable that these GVs encode a gene with properties similar to p74.

Large deletions which remove this p74 gene and the nearby p10 gene result in a virus which produces polyhedra which are not infectious when fed to larvae. Since deletions in the p10 gene alone result in the production of orally infectious polyhedra, deletion of the p74 gene is considered to be responsible for this phenotype (15).

Figure 3:
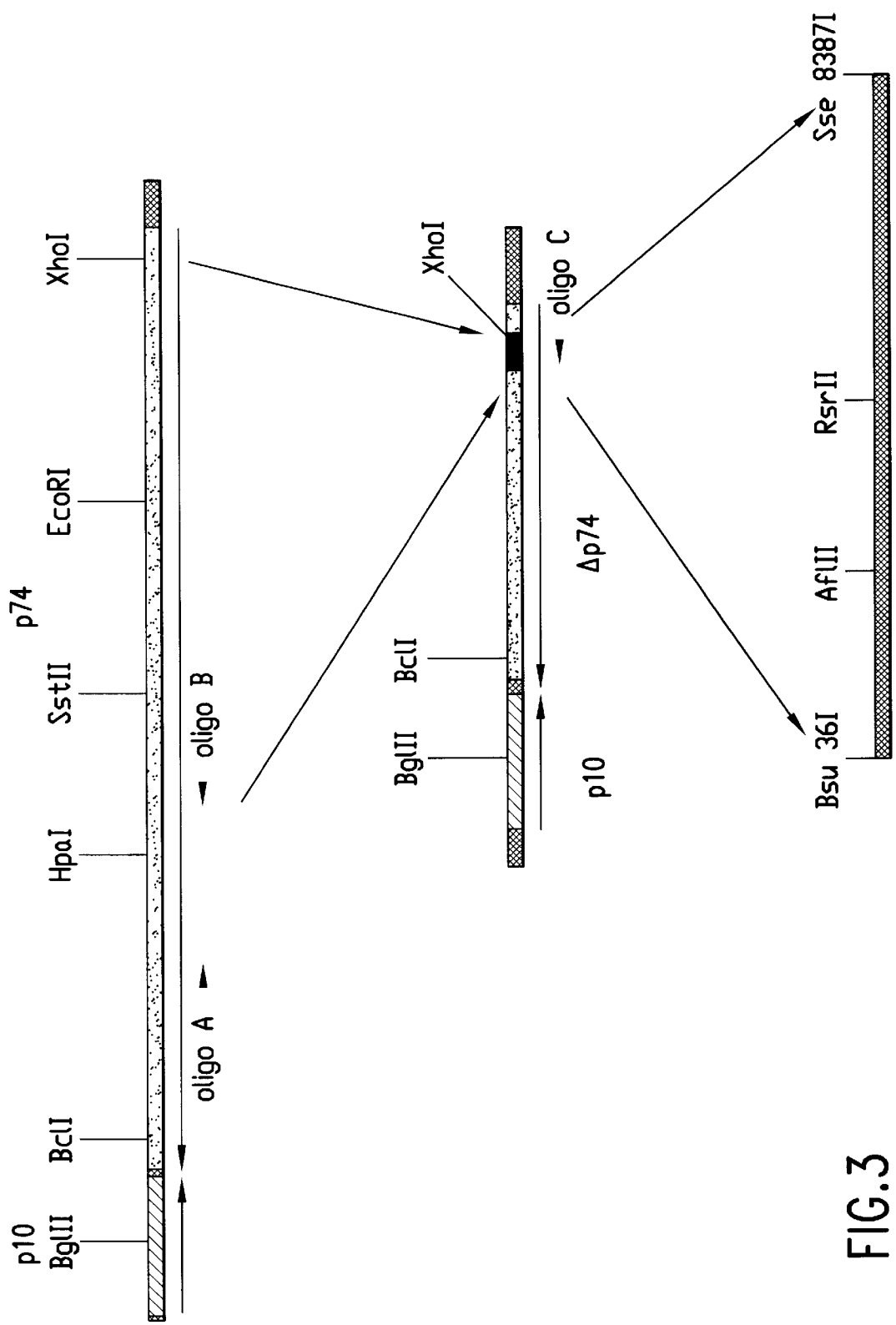
FIG. 3 depicts detail of the deletion in the p74 gene (Δp74) of the AcMNPV A4000 strain.

As described in Example 1 below, applicant has now created a transfer vector (designated Δp74-1) which, when recombined with a wild-type genome, results in a deletion in the p74 gene alone (Δp74) (FIG. 3). Samples of an *E. coli* strain HB101 harboring this transfer vector Δp74-1 were deposited by applicant on May 21, 1992 with the American Type Culture Collection, 12301 Parklawn Drive, Rockville, Md. 20852, U.S.A., and have been assigned ATCC accession number 68,988. Applicant has also deposited on May 21, 1992 samples of an AcMNPV strain designated A4000 (in which the p74 gene has been disrupted by means of a deletion), with the American Type Culture Collection, and have been assigned ATCC accession number VR2373.

The applicant has confirmed, as described in Example 2 below, that it is the deletion of the DNA segment encoding the p74 gene that results in PIBs which are non-infectious when fed to larvae. Budded virus is still produced and is infectious when injected into the hemocoel of the insect.

Simple deletion of a DNA segment is not the only type of alteration used to destroy the function of a target genetic element of the virus. For the purposes of this application, a genetic element is not limited to genes that code for trans-acting substances, such as RNA or protein molecules, but also include cis-acting elements or regulatory sequences, such as transcriptional enhancers, promoters, other transcriptional, translational and genome replication control elements, and viral DNA (or RNA) packaging sequences.

The alteration also takes the form of a frame shift, an insertion, a rearrangement, a point mutation, or other types of disruption of gene function. Included is a frame shift which either prematurely terminates the protein or results in an altered non-functional protein. Insertion of a termination codon into the protein coding region of the gene and placement of the gene for the appropriate suppressor tRNA in the "helper" cell line is also within the scope of the invention.

Other forms of alteration include methods which interfere with viral function, such as suppression of transcription or translation, use of an antisense RNA, insertion of an additional genetic element into the viral genome, and providing the required regulatory element in trans. One example of this method is the use of the yeast upstream-activating sequence dependent on the GAL 4 protein ($UAS_{GAL}$).

Placement of the GAL 4 responsive yeast upstream activating sequence ($UAS_{GAL}$) upstream of the targeted viral gene makes transcription of the viral gene dependent upon the presence of the GAL 4 protein. A "helper" cell line contains the coding region for the GAL 4 gene under control of one of the heterologous promoters described below. Other possible UAS elements are within the scope of this invention, such as those in the yeast mating type system. Also included are regulatory sequence elements which require the binding of a protein for activation, such as steroid receptors and their DNA binding sites.

Also included is the use of promoters which function only in the presence of specific proteins. one example is the T7 promoter of bacteriophage T7, which requires the T7 specific RNA polymerase in order to initiate transcription. Placement of the T7 promoter upstream of the p74 gene in place of its natural promoter makes transcription of the viral gene dependent upon the presence of the T7 RNA polymerase. A "helper" cell line for this virus contains the T7 RNA polymerase under the control of a heterologous promoter such as the IE-1 viral promoter.

In addition to p74 and its functional homologs, there are additional gene functions which, when altered, result in containment of the recombinant virus (e.g., 14). Especially useful are genes involved in functions essential to production of intact, infectious OBs. Examples include a genetic element involved in the regulatory switch from the production of ECVs to OBs, a gene encoding a function required to direct assembly or maturation of the viral particle, and a gene encoding a structural protein of the viral particle.

Further examples of genes that are altered in accordance with this invention include genes which produce FP (few polyhedra) mutants such as the 25K gene (18), as well as genes whose functions lead to the desired phenotype when disrupted, such as viral transcription factors specific for late and very late gene functions, genes for the polyhedron envelope proteins (32–36.5 kD), the gene for a PDV protein which interacts with a midgut receptor and is responsible for the initial infection of midgut cells, a gene or genetic element responsible for assembly of the PDV nucleocapsid, a gene which is responsible for the organization of the polyhedron, and the gene coding for the NPV functional equivalent of the Viral Enhancing Factor (19) found in a GV.

Although the polyhedrin gene is also amenable to alteration, significant practical limitations to its use may exist. The high rate of transcription/translation of the polyhedrin gene, coupled to the great amplification of the viral genome which takes place in virus replication, results in the amount of polyhedrin protein reaching 50–75% of the total stainable protein in the infected cell. This large amount of protein may make it unlikely that a limited number of extraviral copies of the polyhedrin gene could compensate for a deleted viral polyhedrin gene. However, complementation of a polyhedrin-minus virus should be acheivable through the use of regulatory elements or factors which would only need to be provided at a lower level. Examples include engineering the viral polyhedrin gene to contain a suppressor tRNA or altering the regulatory elements of the polyhedrin gene and growing the virus in the appropriate "helper" cell line or insect strain as described above.

In contrast to the polyhedrin gene, the p74 protein appears to be required at a much lower level. Although the gene is transcribed late in viral infection when the viral genome has been grossly amplified, the level of p74-specific mRNA is relatively low. It should be possible to engineer a p74 construct so that a limited number of extraviral copies could provide sufficient p74 function for complementation of the virus to oral infectivity.

The invention is exemplified with AcMNPV. A gene performing a homologous function to the p74 gene should be present in all viruses belonging to the NPV and GV groups of baculoviruses. In species of baculoviruses closely related to AcMNPV, it is possible to identify p74 gene homologs by hybridization with an AcMNPV p74 fragment under conditions of reduced stringency. This approach is especially feasible because available data indicates that the p74 gene is one of the more highly conserved of baculoviral genes (16). For more distantly related viruses, such as the GVs, this approach may not work. An alternative approach for identifying genes encoding a homologous function to an identified AcMNPV gene is described in Example 14. In this set of experiments, an AcMNPV strain with a known genetic defect is cotransfected along with fragments of the viral genome of interest. Complementation of the defect identifies the gene of interest. This approach has been used successfully to identify a gene in Cydia pomonella granulosis virus with a function homologous to the p35 apoptosis inhibiting gene of AcMNPV (20).

Other methods can be used to identify additional essential late gene functions. Passarelli and Miller (21) have recently published a method for identifying transcription factors for late/very late genes. In this method, fragments of the AcMNPV viral genome are cotransfected along with constructs which use late or very late viral promoters to drive expression of the CAT gene. Fragments of the AcMNPV genome which contain genes involved in the normal transcription of viral late/very late genes are identified by their stimulation of CAT activity above background levels.

An insect infectious form of the virus is produced by supplying the altered gene function through the technique of genetic complementation. This insect infectious form of the altered virus is not readily transmissible from host-to-host. Genetic complementation refers to the ability of a gene to convert a mutant phenotype to the wild-type phenotype when present in trans.

Various methods of producing the insect infectious form of the recombinant insect virus are included within the scope of this invention, namely: (1) production in insect tissue culture cells transfected with a fragment of DNA which provides the product or function which is missing from or defective in the altered virus; (2) production in insect cell lines which have been stably transformed with a fragment of DNA which provides the product or function which is missing from or defective in the altered virus; and (3) production in transgenic insects which contain a fragment of DNA which provides the product or function which is missing from or defective in the altered virus. The cell line used in method (1) or (2) provides the missing function and thus serves as a "helper" cell line.

For example, the p74 gene in AcMNPV is deleted as described above. The wild-type p74 gene complements the deficiency of the altered virus in specific embodiments of the three methods just described above as follows: (1) The virus is grown in insect cells which contain extrachromosomal copies of the functional p74 gene. These extrachromosomal copies may be DNA fragments, plasmids containing the p74 gene, or plasmids capable of replication during cell division or in response to viral infection. (2) The virus is grown in an insect cell line with one or more functional copies of the p74 gene stably integrated into the cellular genome. (3) The virus is grown in a transgenic insect which contains one or more functional copies of the p74 gene in the insect genome.

In all three methods, the functional p74 gene can be supplied from AcMNPV, or from any other member of the Family Eubaculoviridae, as long as it restores infectivity. The key concept is that the functional p74 gene is present in trans and provides a diffusible substance that regenerates the wild-type phenotype.

In one method for producing the complemented form of the virus, the virus is grown in a cell line which provides the missing function. For example, the Δp74 virus is produced in a cell line which expresses the p74 gene product. By cotransfecting a plasmid containing the Hind III fragment "P" of AcMNPV—primarily the p74 gene plus a small amount of native flanking sequences of the AcMNPV genome—along with the Δp74 virus, the regeneration of the infectious form of the virus is achieved on a transient basis. Samples of an *E. coli* strain HB101 harboring this plasmid designated AC0028.3, which contains the p74 gene and the flanking sequences just described, have been deposited by applicant on May 21, 1992 with the American Type Culture Collection and have been accorded ATCC accession number 68,987. Because only 0.1–5.0% of the cells in this cotransfection method contain both the functional p74 gene and the Δp74 viral genome, this method is inherently inefficient.

A more efficient method of creating a "helper" cell line is to insert a copy of the p74 gene into the cell, so that the gene is stably integrated into the cellular genome (see Example 6). This procedure has been used to insert non-baculoviral genes into the Sf9 insect cell line (22). The Sf9 insect cell line (ATCC accession number CRL 1711) is a derivative of *Spodoptera frugiperda* 21 (Sf21). A plasmid containing a copy of the gene of interest is cotransfected along with a plasmid containing a selectable marker.

A selectable marker is a gene whose expression permits the identification of cells which have been transformed with a vector containing the marker gene, as well as the gene of interest. Examples of commonly-used selectable markers include the thymidine kinase (TK) and the hypoxanthine-guanine phosphoribosyl transferase (HGPRT) genes, as well as genes which confer resistance to antibiotics, such as neomycin and hygromycin.

A 2- to 20-fold molar excess of the complementing DNA to the DNA containing the selectable marker is used. This maximizes the likelihood that a cell which expresses the selectable marker also contains the gene of interest. The cell line of choice must be permissive for the virus being used. In a preferred embodiment with AcMNPV, the cell line is Sf9 or Sf21. After transfection, the cells are grown under selection and cells which express the selectable marker are amplified. These cell lines are screened for their ability to complement the p74 deletion in the Δp74 virus.

This method is used to isolate Sf9 cell lines which contain copies of the plasmid AC0028.3, a p74-containing plasmid described above. Samples of a cell line designated Sf9(28.3) CL-2, which contains copies of the plasmid AC0028.3 stably integrated into the cellular genome, have been deposited by applicant on Apr. 7, 1993 with the American Type Culture Collection and have been accorded ATCC accession number CRL 11,322. Applicant has confirmed, as described in Example 7 below, that growth of the defective non-orally infectious Δp74 virus in the above cell line results in the production of orally infectious Δp74 virus.

Complementation is not limited to growth of the virus in cell culture. Just as a "helper" cell line can be created, so too a "helper" insect strain can be produced. For example, P element transformation of Drosophila is now routine and a similar system may be designed for any insect. In addition, vectorless transformation of insects is accomplished using techniques similar to those used in mammals. Direct injection (23) or ballistic transformation (24) of pre-blastoderm eggs with metal filaments may be used to create insects carrying the necessary gene.

The relatively weak endogenous p74 promoter is sufficient for production of the p74 gene product. However, it may be preferable to use a stronger or an earlier promoter to drive production of the p74 gene. Use of a heterologous promoter could improve the efficiency of the complementation of the Δp74 virus. Any number of viral promoters are suitable for use. Examples include the 6.9K (basic protein) promoter, the DA26 promoter, the polyhedrin promoter, the 35K promoter, the 39K promoter, the p10 promoter and the IE-1 promoter.

The use of heterologous promoter constructs, such as those described in Examples 4 and 5, has an added benefit. In these constructs, almost all the homologous sequences 5' to the deletion in the p74 gene in the A4000 Δp74 virus described in Example 1 are removed. This should greatly reduce any chance of homologous recombination taking place between the Δp74 virus and the p74 sequences integrated into the cellular genome. This homologous recombination could otherwise result in the restoration of p74 function and a wild-type phenotype to the virus (see discussion in Example 7). A further step to reduce the possibility of homologous recombination is to increase the size of the deletion in the p74 gene of the Δp74 virus so that no coding sequence remains. This is readily accomplished by modifying the protocol in Example 1.

The heterologous promoter is not limited to viral promoters. Cellular promoters are also suitable. There is an unlimited choice of cellular promoters. Examples include the *Bombyx mori* actin promoter and the *Drosophila melanogaster* hsp 70 promoter. Good promoters express at moderate to high levels in the appropriate insect cells during viral infection. These characteristics do not limit one to insect promoters. Various vertebrate, yeast, or promoters from other classes of viruses may fit these criteria. Any of the above mentioned promoters also drive the expression of the selectable marker.

In a further embodiment of this invention, a heterologous gene for an insect controlling or modifying substance is inserted into the viral genome. The substance, for example, is a toxin, a neuropeptide or a hormone, or an enzyme. In particular, the heterologous gene is inserted directly at the site of alteration of the genetic element of the virus, which means that recombination between the genetically altered virus and a superinfecting wild-type virus in most cases will not generate a virus with wild-type function and the inserted heterologous gene. Also within the scope of this invention is insertion of the heterologous gene adjacent to the site of alteration of the genetic element of the virus, such that segregation of the heterologous gene and the altered genetic element occurs in less than 10% of the viral progeny. Containment of the genetically engineered virus is therefore maintained in both cases.

Such toxins include the insect-specific toxin AaIT from the scorpion *Androctonus australis* (25), a toxin from the mite species *Pyemotes tritici* (2), the *Bacillus thuringiensis* subsp. *aizawai* (BTK) toxin (4), a toxin isolated from spider venom (26) and the *Bacillus thuringiensis* CryIVD (BTI) toxin (3). Examples of such neuropeptides or hormones which may be amenable to this procedure include eclosion hormone (6), prothoracicotropic hormone (PTTH), adipokinetic hormone, diuretic hormone and proctolin (5). An example of such enzymes is juvenile hormone esterase (JHE) (7).

For example, a recombinant baculovirus which has a defective or deleted p74 gene and also has a heterologous gene coding for a toxin inserted into the site of the p74 gene alteration results in a virus with increased efficacy against a target insect, but which is unable to be transmitted readily from one insect to another in the environment.

An AcMNPV virus is isolated, as described below in Examples 11–12, where the insect-specific scorpion toxin AaIT, under the control of the viral DA26 promoter, is inserted into the site of the deletion in the Δp74 virus A4000. Samples of this virus designated A4001 have been deposited by applicant's assignee on Apr. 7, 1993 with the American Type Culture Collection and have been accorded ATCC accession number VR 2405. Growth of this virus in wild-type Sf9 cells results in the production of non-orally infectious PIBs (as expected). When this virus is grown in the helper cell line Sf9(28.3)CL-2 described above, the resulting PIBs are orally infectious and the infected insects exhibit the contractile paralysis characteristic of the AaIT toxin (see Example 12 below).

Growth of this virus in a cell line or transgenic insect which supplies the functional p74 gene product enables this virus to infect an insect through the gut. However, because there is no further complementation, the natural populations of insects only produce virus defective for oral infectivity. Thus, in the absence of a co-infecting wild-type virus, the life cycle of the recombinant virus ends with this single infection. This is in contrast to published approaches for using baculovirus (2), where, after the infected insect dies, OBs are released into the environment, where they are ingested by other insects and the life cycle of the virus is repeated, such that host-to-host transmission occurs.

Perhaps most importantly in this invention, the placement of the heterologous gene for the toxin, neuropeptide or hormone, or enzyme adjacent to or directly into the site of the alteration of the viral genetic element means that any homologous recombination between this genetically engineered virus and a wild-type virus only regenerates the original parental genotypes.

For example, insertion of a toxin gene into the deleted region of p74 creates a virus which is toxin+/infectious OB–. Recombination with a wild-type (toxin–/infectious OB+) virus will only yield toxin+/infectious OB– and toxin–/infectious OB+ progeny. A recombination event due to homologous recombination which would yield toxin+/infectious OB+ progeny is prevented, because gene deletion and insertion takes place at the same site, rather than far apart at different loci on the viral genome. Therefore, the toxin gene will only be found in viruses which are genetically defective for the production of infectious OBs. This containment of the heterologous gene for the toxin will be maintained and the infectious virus will disappear from the ecosystem more rapidly than a wild-type virus, due to its reduced ability to generate progeny virus.

In order that this invention may be better understood, the following examples are set forth. The examples are for the purpose of illustration only and are not to be construed as limiting the scope of the invention.

EXAMPLES

Standard molecular biology techniques are utilized according to the protocols described in Sambrook et al. (27). Standard techniques for baculovirus growth and production are utilized according to the protocols described in Summers and Smith (28). Furthermore, all references to "named" AcMNPV restriction fragments are based on the physical maps of the E2 strain of AcMNPV published in Summers and Smith (28).

Example 1

Construction Of The Transfer Vector Δp74-1 And The Recombinant Virus A4000

Figure 2:
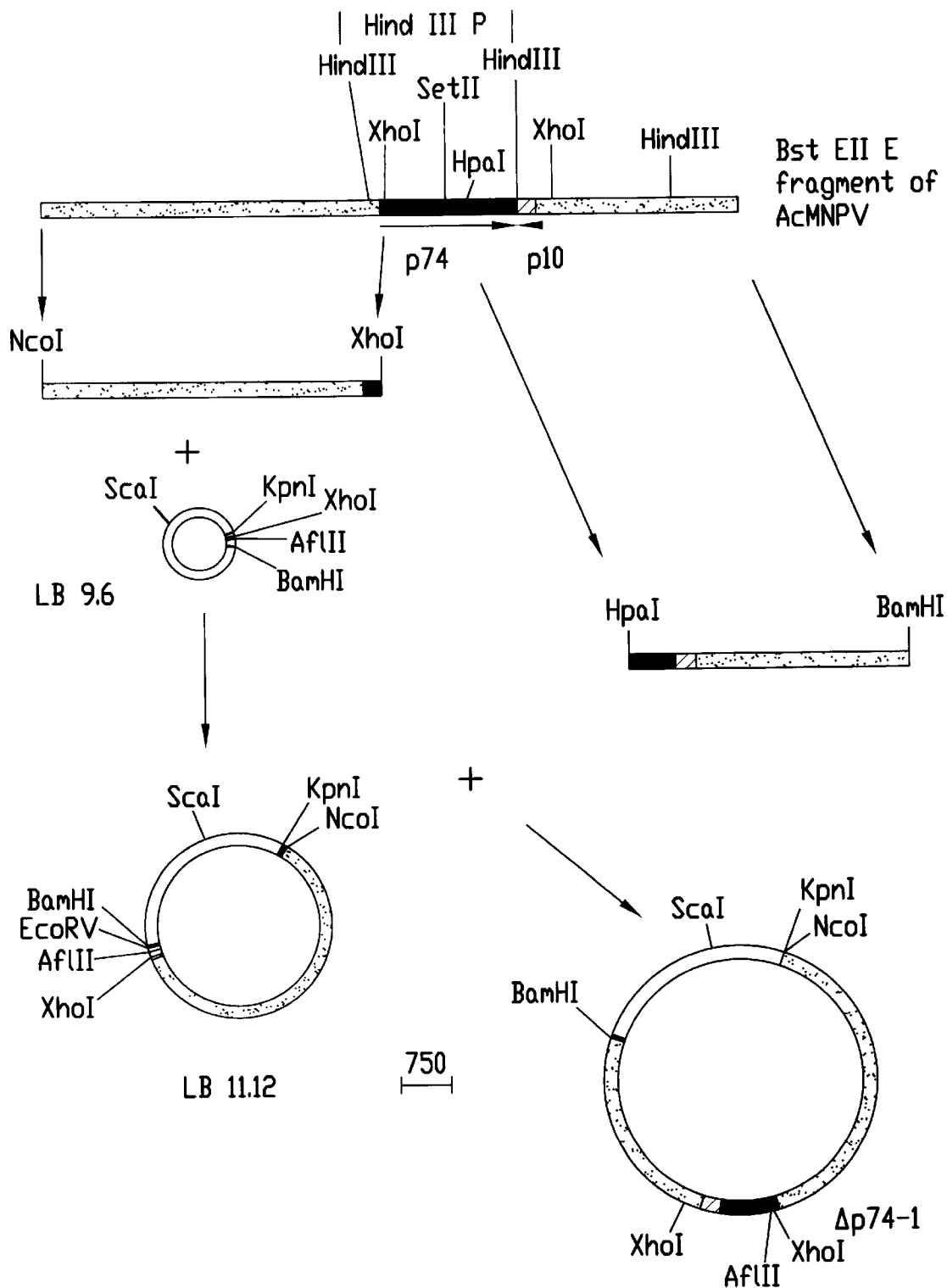
FIG. 2 depicts detail of the construction of the plasmid Δp74-1, which contains a deletion in the p74 gene of AcMNPV.

A transfer vector Δp74-1 is constructed for the purpose of deleting the p74 gene from the E2 strain of *Autographa californica* NPV at approximately map unit 90 of the baculovirus genome (see FIG. 1). The Bst EII fragment "E", which contains the DNA encoding p74, is purified from E2 strain viral DNA. This fragment is subcloned into the Bst EII site of the pSE280 plasmid vector (Invitrogen, San Diego, Calif.). This clone is designated LB10.2. A fragment encoding the 5' region of p74 plus 5' flanking sequences is isolated from LB10.2 by cutting with Nco I, blunting this Nco I site with T4 DNA polymerase, cutting with Xho I and gel purifying the resulting fragment. This Nco I blunted to Xho I fragment is subcloned between the Kpn I site which had been blunted and the Xho I site of the plasmid LB9.6. The plasmid LB9.6 is a derivative of the Bluescript SK plasmid (Stratagene, La Jolla, Calif.), into which a polylinker is inserted at the Hinc II site. The linker contains additional unique restriction enzyme sites useful for the insertion of heterologous genes into the p74 deleted region (see below). The resulting plasmid containing the 5' flanking and 5' p74 sequences described above is designated LB 11.12. An Hpa I to Ban HI fragment of p74 encoding the 3' third of the gene and 3' flanking sequences is isolated and cloned between the Eco RV and Bam HI sites of LB11.12. The resulting clone is the transfer vector Δp74-1 (see FIG. 2). This transfer vector encodes 4750 base pairs (bp) of 5' flanking sequences, p74 sequences from bp 1–69, 64 bp of the plasmid polylinker described above, p74 sequences from bp 1287 to the termination codon at 1937, and 1796 bp of 3' flanking sequence (15). FIG. 3 depicts the deletion in the p74 coding region in more detail. This transfer vector is then used to construct the A4000 strain of the virus by standard cotransfection procedures (29). Two×10$^6$ Sf9 cells are seeded on a 60 mm tissue culture dish. After the cells attach, the media is removed from the cells and replaced with 0.75 ml of Grace's media with 10% fetal calf serum (FCS) plus antibiotics. One μg of AcMNPV DNA plus 2 μg of Δp74-1 DNA are added to 0.75 ml of transfection buffer (25 mM HEPES, pH 7.1, 140 mM NaCl, 125 mM CaCl$_2$). The DNA is then added dropwise to the cells and the cells are incubated for 4 hours at 27° C. After 4 hours, the media is removed and the cells are carefully rinsed with fresh TNMFH plus 10% FCS and antibiotics. The cells are then fed again with fresh TNMFH plus 10% FCS and antibiotics. After 4–5 days, ECV is harvested and individual plaques are isolated by plaque assay as described by Summers and Smith (28).

Individual plaques are then used to infect single wells of a 48 well tissue culture plate which is first seeded with $7.5 \times 10^4$ Sf9 cells in 0.5 ml of fresh TNMFH media. After five days, pools are made from 10 µl of supernatant containing budded virus from each well in either a row or a column. A PCR reaction is set up using 4 µl of the pooled supernatant and oligomers A and C as shown in FIG. 3. Since oligo C is specific to the deleted p74, a fragment will only be amplified in those reactions which contain recombinant virus. The PCR reaction is set up as follows: four µl of the pooled supernatant are first digested for one hour at 55° C. with 200 µg/ml of nonspecific protease from *Streptomyces griseus* (Boehringer Mannheim, Indianapolis, Ind.) in a 25 µl reaction containing 1× Buffer A (10 mM Tris (pH 8.3), 50 mM KCl, 0.1 µg/ml gelatin, 0.45% Nonidet™ P40 (Shell Oil Co.), and 0.45% Tween™ 20 (ICI Americas, Inc.)). The nonspecific protease is then inactivated by heating to 95° C. for 12 minutes. The PCR amplfication consists of mixing the protease treated virus with 50 pmol of each of the specified oligonucleotide primers in a 50 µl reaction containing 200 µM of four dNTPs (DATP, dGTP, dCTP and dTTP), 1.5 mM $MgCl_2$, 1× Buffer A and 1.25 units Ampli-Taq™ DNA polymerase (Perkin-Elmer/Cetus, Norwalk, Conn.). The sample is subjected to 30 cycles of amplification, each consisting of 1 minute at 94° C. (denaturation step), 1.5 minutes at 55° C. (annealing step), and 2.5 minutes at 72° C. (extension step). The 25 cycles are followed by a 7 minute extension step at 72° C. Twenty microliters of the reaction mix is electrophoresed on a 1.2% agarose gel to confirm the presence of recombinant virus. Since the samples are pooled by rows and columns, a recombinant virus is identified by the well which is common to both a positive row and a positive column.

Example 2

Demonstration Of The phenotype Of A4000 In A Leaf Disk Assay On *Heliothis virescens*

A standard leaf disk assay is performed on third instar *Heliothis virescens* larvae to test the infectivity of the A4000 viral strain. A one µl droplet containing virus (with a defined dose of PIBs) in TET buffer (50 mM Tris-HCl, pH 7.5/10 mM EDTA/0.1% Triton™ X-100 (Rohm and Haas, Philadelphia, Pa.)) is added to a 5 mm cotton leaf disk in an individual well containing a premoistened filter paper disk (approximately 4 mm in diameter—30 μl water). After the droplet dries, a single larvae is placed in the well and the well is closed. The larvae are allowed to feed overnight. The next morning, larvae which consume the entire leaf disk are transferred to individual wells containing insect diet. The larvae are monitored for mortality until survivors pupate. This procedure is repeated with a wild-type E2 AcMNPV viral strain designated A1000, which is used as a control. The results of two separate tests are as follows:

| Virus | Dose (PIBs) | # Dead |
|---|---|---|
| Test 1 | | |
| A4000 | $2.5\times10^5$ | 1/31 |
| (Δp74) | $5\times10^4$ | 0/32 |
| | $5\times10^3$ | 0/31 |
| | $5\times10^2$ | 0/32 |
| A1000 | $5\times10^2$ | 16/18 |
| (wild-type) | $5\times10^1$ | 14/31 |
| Test 2 | | |
| A4000 | $5\times10^6$ | 0/20 |
| (Δp74) | $5\times10^5$ | 0/21 |
| | $5\times10^4$ | 0/24 |
| | $5\times10^3$ | 0/20 |
| A1000 | $5\times10^2$ | 22/32 |
| (wild-type) | $5\times10^1$ | 5/32 |

These results demonstrate that the virus containing the p74 gene deletion is not infectious, even at doses 10,000 fold higher than the infectious virus containing the intact p74 gene. The death of one larva seen with A4000 is not believed to be due to the normal route of infection.

Example 3

Complementation Of A4000 To Produce A Noninfectious Form Of The Virus By Growth In A Cell Line Containing A Non-Stably Integrated Copy Of The Hind III Fragment "P" Of AcMNPV Sf9 cells are cotransfected by the standard protocols described in Example 1. One μg of A4000 genomic viral DNA with and without a 10-fold molar excess of AC0028.3 plasmid DNA is used in the transfections. AC0028.3 consists of the Hind III fragment "P" of AcMNPV inserted into the Hind III site of Bluescript KS II (Stratagene, LaJolla, Calif.). The Hind III fragment "P" is indicated at the top of FIG. 2 as a portion of the Bst EII fragment "E" of AcMNPV. This fragment contains the entire p74 coding sequence with 221 bp of 5' flanking and 56 bp of 3' flanking sequence. After 48 hours, polyhedra are harvested from infected cells by low speed centrifugation, followed by resuspension in TET buffer. SDS is added to the resuspended virus to a final concentration of 1%. Cellular DNA is sheared by vigorous mixing and pipetting of the sample. A number of sequential washes of the PIBs in TET buffer without SDS, followed by low speed centrifugation, are used to remove the cellular DNA. Finally, the PIBs are resuspended in TET buffer and counted on a hemocytometer for the assay. A bioassay is conducted as described in example 2. At a dose of $1\times10^5$ PIBs, polyhedra from Sf9 cells transfected with A4000 DNA alone do not result in larval death. PIBs from Sf9 cells cotransfected with A4000 and AC0028.3 DNA result in larval death due to infectious virus. Therefore, growth of the A4000 virus in cells providing functional p74 protein (due to the presence of AC0028.3 plasmid) results in production of insect infectious A4000 virus. This virus is capable of establishing a productive infection in larvae. This result is confirmed by harvesting PIBs from the dead larvae. PIBs are harvested by placing the cadavers in a cup from which the bottom had been removed and replaced with Nytex™, a trademark of Tetko, Briarcliff Manor, N.Y. TET buffer is then washed over the cadavers (1 ml/larva) and flow-through, which contains the PIBs, is collected. These PIBs are resuspended in TET buffer plus 1% SDS, mixed and spun down at low speeds. The PIBs are then washed several times with TET buffer without SDS. DNA is prepared from these PIBs as described at page 35 in Summers and Smith (28). PCR amplification, using the oligomers as described in Example 1, is used to confirm the presence of the Δp74 virus in these dead larvae.

Example 4

Construction Of Expression Vectors Containing A Heterologous Promoter

Figure 4:
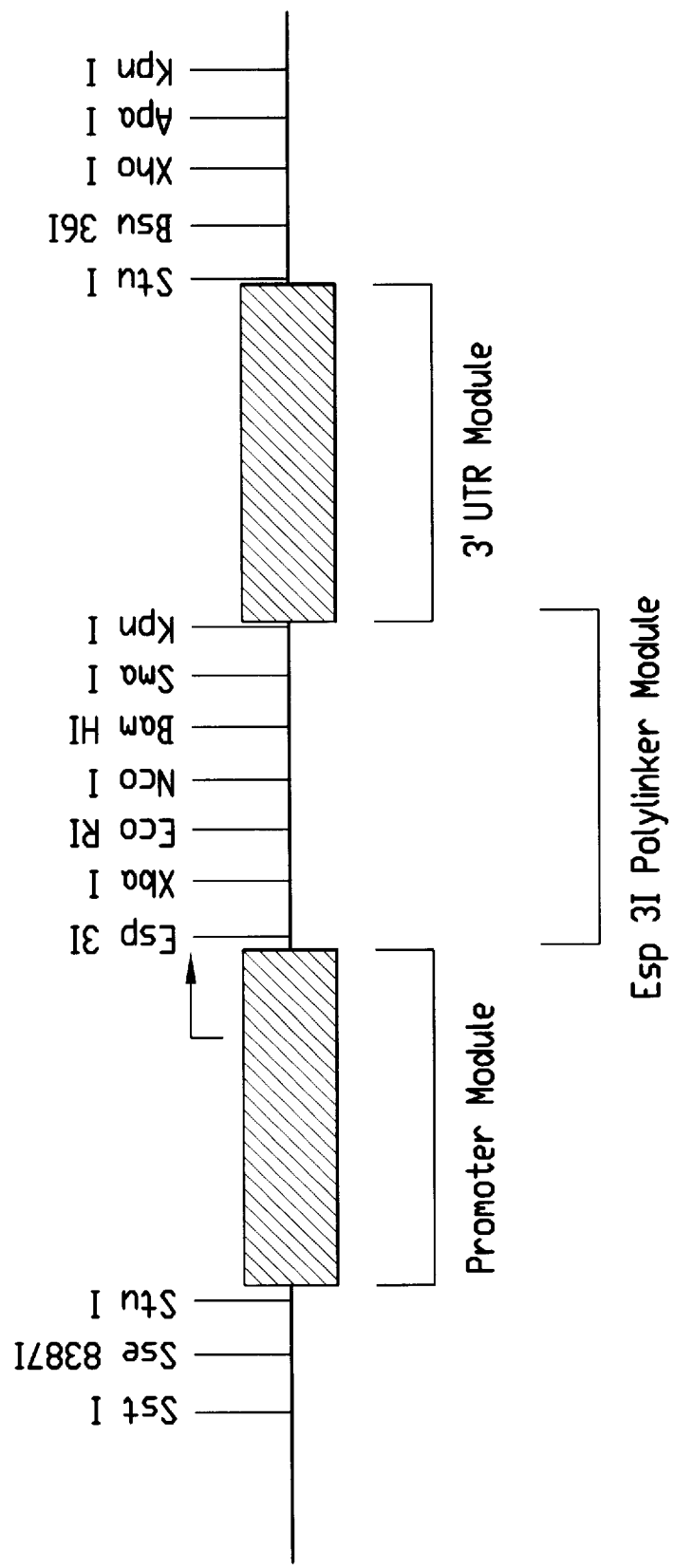
FIG. 4 depicts a restriction map of a portion of an expression vector of the pMEV series showing the promoter, polylinker and 3' UTR.

The use of heterologous promoters to drive the expression of the p74 gene may increase the efficacy of complementation of the Δp74 virus. Convenient expression vectors for this use consist of the following modules: (1) a heterologous promoter module, which is used to regulate transcription; (2) a polylinker module, which facilitates insertion of the DNA sequences whose expression is desired; and (3) a 3' UTR, which provides a site for primary transcript processing and polyadenylation (see FIG. 4). Such an expression vector, which consists of the AcMNPV DA26 gene promoter, a polylinker, and the AcMNPV 6.9 k basic protein 3' UTR, is designated pMEV1. Samples of an *E. coli* DH5$_\alpha$ strain harboring a specific pMEV1 isolate designated AC0064.1 have been deposited by applicant's assignee with the American Type Culture Collection on Apr. 7, 1993, and have been accorded ATCC accession number 69275.

Additional vectors can readily be prepared by substituting the promoter-containing Pst I/Xba I fragment of pMEV1 with Pst I/Xba I-digested fragments containing the AcMNPV 6.9K (pMEV2), polyhedrin (pMEV3) and 35K (pMEV4) viral gene promoters.

The promoter fragments used in constructing these vectors are formed by PCR amplification of cloned viral DNA using promoter-specific pairs of oligonucleotide primers. The primers are designed so that the amplified promoter segments have the following general structure: (1) a 5' terminal 22 bp heteropolymeric synthetic sequence with recognition sites for restriction endonucleases Sst I, Sse 8387I and Stu I (in that order); (2) a segment of viral DNA that extends from a point 100–350 bp upstream of the predominant transcriptional start site of the gene to the 3' terminus of the 5' UTR (that is, position −1 with respect to the translation initiation codon); and (3) a 3' terminal 23 bp heteropolymeric region with recognition sites for restriction endonucleases Esp 3I and Xba I (in that order). The location and orientation of the Esp 3I recognition site places the cleavage sites between positions −5 and −4 in the (+) strand and between positions −1 and +1 in the (−) strand.

The template used to prepare the 35K promoters is the AcMNPV Hind III fragment "K". The sequence of the (+) strand primer contains the 22 bp heteropolymeric sequence with sites for the restriction enzymes Sst I, Sse 83871 and Stu I and 35K 5' sequence from −399 to −382. The (−) strand primer contains 35K 5' sequence from −21 to −1, followed by the 23 bp heteropolymeric region with sites for the restriction enzymes Esp 3I and Xba I. For each amplification reaction, 50 pmol of the appropriate primer pair is mixed with 250 pg of template DNA in a 50 μl reaction mixture containing 10 mM Tris-HCl (pH 8.3), 50 mM KCl, 1.5 mM MgCl$_2$, 200 μM dNTPs, 100 μg/ml gelatin and 2.5 units AmpliTaq™ DNA polymerase (Perkin-Elmer/Cetus, Norwalk. Conn.). The sample is amplified through 25 cycles of 1 minute at 94° C. (denaturation step), 1.5 minutes at 55° C. (annealing step), and 3.0 minutes at 72° C. (extension step). As in other reactions, 7 minutes are added to the last extension step.

Each reaction is terminated by the addition of EDTA to 10 mM and Sarkosyl (sodium N-lauroylsarcosine) to 0.2% (w/v). The products are then extracted once with chloroform, once with phenol:chloroform and precipitated with ethanol. The DNA samples are redissolved in an appropriate buffer and then digested with Pst I (which recognizes the central six basepairs [CTGCA↓ G] of the Sse 8387I site) and Xba I. Each presumptive promoter fragment is then purified by gel electrophoresis on a 1.2% low melt agarose gel and ligated to a 3.2 kb Pst I/Xba I vector fragment prepared from pMEV1. This fragment contains the polylinker module, 3' UTR module and Bluescript SK+ framework of pMEV1. The desired recombinants are identified by restriction enzyme analysis and DNA sequence determination. Persons of ordinary skill in the art can duplicate this procedure for any promoter region whose sequence is available, such as the AcMNPV 6.9K promoter, the polyhedrin promoter, or cellular promoters such as the *Drosophila melanogaster* hsp 70 promoter.

Example 5

Construction Of Heteroloaous Promoter-p74 Coding Region Constructs

The protein coding region of p74 is isolated for insertion into the expression vectors containing heterologous promoters (as described in Example 4) by PCR amplification of the appropriate region of AC0028.3. The 24 bp (+)-strand primer used in this reaction has a 5' terminus at the ATG translation start site of the p74 gene. The (−)-strand primer is 29 bp long and consists of 20 bp of 3' p74 sequence ending with the TAA translation stop codon, followed by 9 bp of additional sequence which includes a Bam HI site. Conditions for PCR consist of mixing 250 pmol of AC0028.3 with 50 pmol of each of the specified oligonucleotide primers in a 50 μl reaction mixture containing 200 μM of each dNTPs (DATP, dGTP, dCTP and dTTP), 1.5 mM MgCl$_2$, 1× Buffer A and 1.25 units AmpliTap™ DNA polymerase (Perkin-Elmer/Cetus, Norwalk. Conn.). The sample is subjected to 5 rounds of amplification, each consisting of 1 minute at 94° C. (denaturation step), 1.5 minutes at 45° C. (annealing step), and 3 minutes at 72° C. (extension step), followed by 25 rounds of amplification, each consisting of 1 minute at 94° C. (denaturation step), 1.5 minutes at 55° C. (annealing step), and 2.5 minutes at 72° C. (extension step). The cycles are followed by a 7 minute extension at 72° C.

After purification, the reaction products are treated with the Klenow fragment of DNA polymerase I (27) in the presence of all four dNTPs to ensure that the PCR products have blunted ends. The 3' end of the p74 coding region is then digested with Bam HI and the resulting fragment is purified by electrophoresis on a 1% low melt agarose gel. This fragment is then cloned into any of several expression vectors described in Example 4. To prepare the expression vectors for p74 gene insertion, each vector is digested with Esp 3I, and the resulting 5' protruding termini are filled in by the action of *E. coli* DNA polymerase I (Klenow fragment) in the presence of all four dNTPs. Each preparation is then digested with BamHI. The vector is separated from the liberated polylinker fragment by electrophoresis on a 1% low melt agarose gel and then ligated in separate reactions to the p74-encoding gene fragment.

Example 6

Isolation Of Stable Sf9 Cell Lines Which Contain A Functional Copy Of The p74 Gene Integrated Into The Cellular Genome In this example, derivatives of Sf9 cells having p74 gene-containing constructs stably inserted into the cellular genome are isolated as described in Jarvis et al. (22). Specifically, a plasmid designated AC0028.3 (ATCC 68,987) is used. This plasmid contains the AcMNPV Hind III fragment "P", which encompasses the p74 gene plus a small amount of native flanking sequences. First, Sf9 cells are cotransfected with a mixture of 2 µg of the AC0028.3 plasmid DNA and 1 µg of the plasmid IE-1 Neo DNA (22). After transfection, the cells are incubated for 2 hours at 28° C. After washing the cells with complete TNMFH media (27), the cells are fed again and incubated for 22 hours at 28° C. The cells are then plated at low density to generate a sparsely seeded culture and fed again with complete TNMFH plus 0.5 mg/ml (on an active ingredient basis) of the neomycin analog G418 (GIBCO-BRL, Grand Island, N.Y.). The cells are then incubated at 28° C. for one week. At the end of one week, the media is changed to complete TNMFH without G418. For each of three separate plates, the following procedure is used. The surviving cells are harvested and amplified. The three amplified sets of cells are stable cell lines designated Sf9(28.3)CL-1, Sf9(28.3)CL-2 (ATCC CRL 11,322) and Sf9(28.3)CL-3. These mixed populations are grown up and then checked for the presence of the p74 gene using PCR, as described in Example 1, with the oligomer specific for the (+) strand of p74 (oligomer A) and an oligomer specific for the region missing from the p74 gene in the A4000 virus (oligomer B) as shown in FIG. 3.

Example 7

Production Of Insect Infectious A4000 Virus By Growth In The Above Cell Lines And Demonstration Of Phenotype Each of the three cell lines isolated as described in Example 6 are infected at an MOI of greater than 1 with the A4000 virus. Production may be carried out at an MOI ranging from about 0.01 to 20. PIBs are harvested from infected cells as described in Example 3. A standard leaf disk assay (see Example 2) is performed. The results of three separate tests are described below, where the A1000 virus is the wild-type E2 strain of AcMNPV:

| Virus/Cell Line (Passage #) | Dose (PIBs) | # Dead/ # Tested | % Mortality |
| --- | --- | --- | --- |
| Test 1 | | | |
| A4000/Sf9 | $1 \times 10^5$ | 0/16 | 0 |
| A4000/CL-1(P3) | $1 \times 10^5$ | 7/16 | 44 |
| A4000/CL-2(P2) | $1 \times 10^5$ | 9/15 | 60 |
| A4000/CL-3(P2) | $1 \times 10^5$ | 6/16 | 38 |
| A1000/Sf9 | $1 \times 10^3$ | 30/32 | 94 |
| Untreated | 0 | 0/30 | 0 |
| Test 2 | | | |
| A4000/Sf9 | $1 \times 10^5$ | 0/15 | 0 |
| A4000/CL-1(P3) | $1 \times 10^5$ | 1/15 | 6 |
| A4000/CL-2(P2) | $1 \times 10^5$ | 4/16 | 25 |
| A4000/CL-3(P2) | $1 \times 10^5$ | 6/16 | 38 |
| A1000/Sf9 | $1 \times 10^3$ | 21/28 | 75 |
| Untreated | 0 | 0/32 | 0 |
| Test 3 | | | |
| A4000/Sf9 | $1 \times 10^5$ | 0/16 | 0 |
| A4000/CL-1(P7) | $1 \times 10^5$ | 5/16 | 31 |
| A4000/CL-2(P6) | $1 \times 10^5$ | 5/16 | 31 |
| A4000/CL-3(P6) | $1 \times 10^5$ | 0/16 | 0 |
| A4000/CL-3(P2) | $1 \times 10^5$ | 3/15 | 20 |
| A1000/Sf9 | $1 \times 10^3$ | 17/31 | 55 |
| Untreated | 0 | 0/15 | 0 |

As can be seen from this data, when Sf9 cells stably transformed with the plasmid AC0028.3 are infected with A4000 virus, the resulting PIBs are now orally infectious. In contrast, PIBs from A4000 infected parental, nontransformed Sf9 cells do not result in larval death. This signifies that growth of the A4000 virus in cells providing functional p74 protein (due to the stable integration of a functional p74 gene construct as described in Example 6) results in production of insect infectious A4000 virus. The reason for the loss of complementation in passage 6 of the Sf9(28.3)CL-3 cell line is not known.

DNA is next prepared (as described in Example 3 and page 35 of Summers and Smith (28)) from PIBs individually harvested from twenty larvae killed by the complementing virus in Test 1 above. PCR amplification using primers A and C to assay for the presence of Δp74 virus, and primers A and B to assay for the presence of wild-type virus (see FIG. 3 for primers) is carried out as described in Example 1. The results demonstrate that all twenty larvae are infected with Δp74 virus. In addition to a positive signal for the Δp74 virus, five of the twenty larvae exhibit a strong PCR band specific for the presence of an intact p74 gene. A leaf disk assay (see Example 2) is performed using PIBs isolated from 18 of the twenty larvae from Test 1. A dose of $1 \times 10^5$ PIBs/larva and 32 test larvae are used for each sample. Only the four larvae examined having a positive signal for the presence of an intact p74 gene produce mortality above background levels. None of the 14 examined which test positive solely for the presence of the deleted p74 gene cause larval mortality above background levels.

Without being bound by the following, these results should be due to one of two causes. The more direct reason could be that samples of the complemented virus are contaminated with wild-type virus or that some of the larvae from the initial test (Test 1) harbor wild-type virus and, when superinfected with Δp74 virus, both wild-type and Δp74 virus could be present in the PIB preparations from these larvae. An alternative explanation could be that, during growth of the Δp74 virus in the complementing cell line, homologous recombination occurs between the virus and the p74 sequences integrated in the cellular genome. If this occurs at a low level, then only some of the larvae which die from complemented virus would also contain wild-type virus. This wild-type virus would be orally infectious in the second round of assays. In the present constructs, 284 bp of homology exists between the Δp74 virus and the p74 sequences integrated in the cellular genome 5' of the deletion and 713 bp of homology exists 3' to the deletion. If the alternative explanation is correct, then this result can be avoided by decreasing or, if necessary, eliminating the amount of homologous sequence present between the virus and the cell line.

Example 8

Construction Of Transgenic Insects Which Contain A Functional Copy Of The p74 Gene Stably Integrated Into The Insect Genome In this example, ballistic introduction of DNA via tungsten particles is used to construct transgenic insect strains (24). 20–100 µg of DNA for one of the p74 constructs described in Example 5, in embryo injection buffer (0.1 mM sodium phosphate, pH 6.8, 5 mM KCl), is precipitated onto 1.2 mm diameter washed tungsten particles (Bio-Rad, Richmond, Calif.). The total volume of the precipitation reaction is 65 µl. After the precipitation, 50 µl of supernatant is removed. The pellet and 12–15 µl of supernatant are vigorously mixed just before applying 8 µl to the macro-projectile. A Biolistics bioparticle delivery system (DuPont, Wilmington, Del.) is used to bombard dechorionated *Trichoplusia ni* embryos prior to the formation of the blastoderm. During this procedure, the embryos are supported on filter paper. The embryos are then placed under Series 700 halocarbon oil (Halocarbon Products Corp., Hackensack, N.J.) until hatching. When surviving insects hatch, groups of 25 insects are placed in cages together. Eggs are collected from these cages and DNA is prepared from the embryos as described in Roberts (30). A PCR reaction (see Example 1), using oligomers A and B as shown in FIG. 3, is conducted to determine which cage is producing eggs containing the p74 gene. Once positive groups are identified, eggs from that group are placed on diet and allowed to develop into adults. Individual pairs of adults are mated and DNA isolated from the eggs they produce is again assayed by PCR for the presence of the p74. This process continues until a line of moths is established that is homozygous for the p74 gene.

Example 9

Production Of Insect Infectious A4000 Virus By Growth In The Above Transgenic Insect Strains And Demonstration Of The Phenotype Initially, 5 μl haemolymph injections of $1\times10^5$ A4000 budded virus in tissue culture media are given to a small number (10–20) of fourth instar transgenic *Trichoplusia ni* larvae. After deaths due to the A4000 virus are noted in a majority of the larvae (4–5 days), PIBs are harvested as described in Example 3. These PIBs are then used for further amplification. Third instar transgenic *Trichoplusia ni* larvae containing one of the p74 constructs described in Example 5 are fed on 1×1.5 inch rectangles of diet which is surface contaminated with 0.4 μl of $1\times10^6$ PIBs/ml A4000 virus. When deaths due to the A4000 virus are noted in a majority of the larvae (5–6 days), PIBs are harvested as desribed above. A sample of these PIBs is stored in TET buffer as a stock and the virus is then bioassayed in a standard leaf disk assay on wild-type second instar *Trichoplusia ni* larvae. Results demonstrate that growth of A4000 in transgenic insects containing a functional p74 gene restores insect infectivity of the virus at approximately normal levels. However, the virus harvested from the wild-type larvae killed by this complemented virus has a reduced capacity to orally infect insects.

Example 10

Insertion Of A Gene Encoding A Toxin Into The Δp74-1 Transfer Vector And Isolation Of The Recombinant Virus A4TxP-I A DNA fragment encoding the insect-specific mite toxin from *Pyemotes tritici* (TxP-I) is isolated from the cDNA clone Tox34 (2). An Eco RI fragment containing the entire protein coding region of the gene plus some 5' and 3' untranslated region is cloned into the AcMNPV pVL 1393 vector (Invitrogen, San Diego, Calif.). An Eco RV to Hind III (blunted) fragment from this construct is inserted into the transfer vector Δp74-1 at the Afl II site, which is internal to the deletion (see FIG. 2). Cotransfection of this plasmid, designated LB15.9, with A4000 viral genomic DNA onto Sf9 cells, as described in Example 1, results in a recombinant virus which encodes the TxP-I gene, but which cannot orally infect larvae. Injection of the budded form of this virus into the haemolymph of fourth instar *Heliothis virescens* larvae does result, however, in the characteristic paralysis caused by expression of TxP-I. In addition, growth of this virus by the methods described in Examples 3, 7 and 9 results in the production of insect infectious A4TxP-I virus. This infectious A4TxP-I virus can orally infect larvae and induce paralysis. However, the virus produced by these infected larvae does not retain its insect infectivity.

Example 11

Construction Of An Expression Vector Containing A Codon Optimized AaIT Gene

An insect-specific toxin, AaIT, is found in the venom of the North African scorpion *Androctonus australis* Hector. A transfer vector for the insertion of the AaIT gene into the polyhedrin gene region of AcMNPV is constructed. This vector, designated AC0055.1, contains the AaIT gene inserted into the BamHI site of pVL985 (30), and consists of a codon optimized nucleotide sequence for the mature AaIT toxin, linked to the signal peptide of a *Drosophila melanogaster* cuticle gene. Samples of an *E. coli* strain HB101 harboring this transfer vector AC0055.1 have been deposited by applicant's assignee on Dec. 17, 1992 with the American Type Culture Collection and have been assigned ATCC accession number 69,166.

The toxin coding segment of this transfer vector is recovered for subsequent insertion into the expression vectors of Example 4 by PCR. The (+)-strand primer used for the reaction is an oligonucleotide of 27 bases, whose 5' terminus coincides with the ATG translation initiation codon of the codon optimized AaIT gene (in AC0055.1) to be amplified.

The (−)-strand primer hybridizes to a site in AC0055.1 located about 35–40 bp downstream of the 3' terminus of the AaIT gene. The conditions for the PCR reaction are essentially as described in Example 1. After purification, the reaction products are treated as described in Example 5, except that the fragment is purified by electrophoresis on a 1.8% low melt agarose gel.

To prepare the expression vectors for toxin gene insertion, each vector is digested with Esp 3I, and the resulting 5' protruding termini are filled in by the action of *E. coli* DNA polymerase I (Klenow fragment) in the presence of all four dNTPs. Each preparation is then digested with BamHI. The vector is separated from the liberated polylinker fragment by electrophoresis on a 1% low melt agarose gel and then ligated in separate reactions to the AaIT-encoding gene fragment.

Example 12

Isolation Of The AaIT Toxin-Encoding Recombinant A4001 Virus

To prepare A4000 viral DNA for gene insertion, the DNA is linearized by sequential digestions with Sse 8387I and Bsu 36I. In a typical preparation 40 μg of A4000 viral DNA is digested for 2 hours at 37° C. with 100 units of Sse 8387I (Takara Biochemical, Inc., Berkeley, Calif.) in a 250 μl reaction containing 10 mM Tris-HCl, pH 7.5, 10 mM MgCl$_2$, 1 mM dithiothreitol (DTT), 50 mM NaCl, and 0.01% BSA. The reaction mixture is then adjusted to 100 mM NaCl and 50 mM Tris HCl, pH 7.9, and the DNA is digested for 2 hours at 37° C. with 100 units of Bsu 36I (New England Biolabs, Beverly, Mass.). The reaction is then terminated by adding SDS to a final concentration of 1% (w/v), NaCl to a final concentration of 0.3 M and EDTA to a concentration of 10 mM. Thereafter, the DNA is chromatographed on a "poly-prep" column (BioRad Laboratories, Richmond, Calif.) containing a 2 ml bed volume of Sephacryl-300 (Pharmacia, Piscataway, N.J.), equilibrated with 10 mM Tris-HCl (pH 8.0), 1 mM EDTA, 0.1% SDS, and 0.3 M NaCl. Twelve 150 μl fractions are collected. Ten microliters of each fraction are analyzed by gel electrophoresis to identify fractions containing the viral DNA. These fractions are pooled, extracted once with phenol:chloroform, and the viral DNA is then precipitated with ethanol. The DNA is resuspended in TE (10 mM Tris-HCl (pH 8.0), 1 mM EDTA) at a concentration of 0.2–1 mg/ml and stored at 4° C. To determine if the viral DNA has been linearized completely, an aliquot is digested with Eco RI and analyzed by gel electrophoresis. Viral DNA exhibiting a 7 kb Eco RI fragment has not been digested completely with Bsu 36I and Sse 8387I and is not used.

The AaIT-containing expression vector described in Example 11 is digested with Bsu 36I and Sse 8387I. Twelve ng of toxin-encoding fragment is ligated with 0.5 μg of the Bsu36I/Sse 8783I-linearized and purified AcMNPV A4000 DNA in a 5 μl reaction mixture containing 25 mM Tris-HCl (pH 7.6), 5 mM $MgCl_2$, 1 mM ATP, 1 mM DTT, 5% (w/v) polyethylene glycol-8000, and 0.5 units T4 DNA ligase (Gibco-BRL, Gaithersburg, Md.). After an overnight incubation at 16° C., the entire ligation reaction is used to transfect Sf9 cells, as described in Example 1.

Five days after transfection, the media is removed from the transfected Sf9 cells. Ten-fold serial dilutions of the transfection supernatant are prepared and two 1 ml aliquots of the $10^{-3}$, $10^{-4}$ and $10^{-5}$ dilutions are used to infect $1.5 \times 10^6$ cells in a 6 cm culture dish. One hour after addition of virus, the virus inoculum is removed and the cells are overlaid with agarose-containing medium, as described in the preceding example. When plaques have fully developed, they are used to inoculate individual wells of a 48 well plate and the resulting progeny viruses are assayed by PCR using primer A in FIG. 3 as the (+)-strand primer and the (−)-strand cuticle-AaIT primer described in Example 11.

After one or two additional rounds of plaque purification, P1 stocks are prepared (28). The AaIT-containing recombinant virus is designated A4001. The biological activity of this virus is assayed by performing an injection assay on the ECV. The ECV is injected into mid-fourth instar *Heliothis virescens* (tobacco bud worm) larvae. The virus is titered by the plaque assay method (28), and then diluted to $2 \times 10^7$, $2 \times 10^6$, and $2 \times 10^5$ PFU/ml in TNM-FH medium supplemented with 0.5% (v/v) red dye number 5. Each larva is anesthetized with carbon dioxide for 2–5 minutes and then injected with 0.5 μl of diluted virus, using a Hamilton syringe equipped with a 26 gauge needle. The needle is inserted longitudinally between the last two prolegs and then moved anteriorly two to three body segments prior to injection. Following injection, each larva is inspected for the release of dye-stained hemolymph and discarded if sample loss is evident or suspected. The larvae are then stored at 27° C. in covered 4 $cm^2$ diet cells (one larva per cell) and inspected visually once daily for evidence of morbidity or mortality. An individual is scored as moribund (positive response) if it is unable to right itself within 0.5–2 minutes after being turned on its back.

When *H. virescens* larvae are injected with $6 \times 10^3 – 1 \times 10^4$ PFU of the virus, larvae responding to the A4001 viral infection exhibit the contractile paralysis and decreased response time compared to wild-type AcMNPV characteristic of AaIT-producing recombinant virus. Specifically, the recombinant virus has a mean response time ($RT_{50}$) of 50% (+/−4%) of the value for the wild-type virus in one bioassay, and an ($RT_{50}$) of 52% (+/−5%) of the value for the wild-type virus in a second bioassay. This result shows that insertion of the AaIT gene and the cuticle signal sequence into AcMNPV (A4001) accelerates the speed of kill through the expression of biologically active toxin.

In a standard leaf disk assay, as described in Example 2, only larvae fed A4001 virus grown in the rescuing cell line Sf9(28.3)CL-2 exhibit the contractile paralysis characteristic of the AaIT toxin. In contrast, larvae fed A4001 virus grown in wild-type Sf9 cells exhibit no contractile paralysis.

Example 13

Construction Of The Transfer Vector $UAS_{GAL}$-$p^{74}$ And The Virus A4UAS

In this example, a specific yeast upstream activating DNA sequence, $UAS_{GAL}$, plus a minimal *Drosophila melanogaster* hsp 70 promoter (−43 to −1 bp), is inserted at −1 bp upstream of the p74 coding region in the virus. The GAL4 structural gene is isolated from the pLA plasmid (32) as a 2.9 kb Bam HI to Hind III fragment. This GAL4 fragment is inserted into one of the vectors containing a heterologous promoter as described in Example 5. Stable Sf9 cells which contain functional copies of the heterologous promoter-GAL4 constructs are isolated as described in Example 6. In order to generate the $UAS_{GAL}$-p74 recombinant virus, a $UAS_{GAL}$-p74 transfer vector is constructed. The 17-hsp 70/lacZ construct (33) is used as the substrate for PCR to generate a 175 bp fragment. This fragment consists of four copies of a 29 bp repeat which contains the high affinity 17mer GAL4 recognition site fused to a minimal *Drosophila melanogaster* hsp 70 promoter (−43 to −1 bp). Specific primers are used which add restriction sites required for subsequent cloning steps to the 5' (Sma I) and 3' (Esp 3I and Nde I) ends of this fragment. This fragment is inserted into the Δp74-1 transfer vector (see FIG. 4) between the 5' most Hind III which has been blunted and the Nde I site of the p74 gene. This plasmid clone is designated LB 17.8. The p74 coding region fragment is generated by PCR amplification using the (+) strand p74-specific primer as described in Example 5 and the Bluescript-specific primer T3 (Stratagene, LaJolla, Calif.) to prime the (−) strand. This p74 fragment is treated with the Klenow fragment of DNA polymerase I as described previously. After purifying the fragment, it is digested with Bcl I which cuts near the 3' end of the p74 gene. LB 17.8 is prepared similarly by digestion with Esp 3I, followed by blunting of this end with Klenow. After purifying the vector, it is also digested with Bcl I. The prepared vector and the p74 gene fragment are then ligated together under standard conditions. This clone is designated $pUAS_{GAL}$-p74 and contains a complete p74 gene under the control of the hsp promoter, but dependent upon the presence of the Gal4 protein. A recombinant AcMNPV virus designated A4UAS is generated by the method described in Example 1. Complemented virus is produced by growing this recombinant virus in the cell lines described in Example 6. A standard bioassay as described in Example 2 is performed and results demonstrate that the $UAS_{GAL}$-p74 is non-infectious to insects when fed orally, but that when this virus is grown in the GAL4 complementing cell line, it is infectious to insects by oral feeding.

Example 14

Isolation Of A Functional Analog To The AcMNPV p74 Gene From The Genome Of A Granulosis Virus Isolation of a gene responsible for the oral infectivity of a granulosis virus is feasible using the technique of marker rescue (21). A genomic library of overlapping cosmid clones is first prepared from viral DNA of the *Trichoplusia ni* granulosis virus (TnGV) by ligation of a partial Sal I digest of TnGV DNA into the cosmid vector pVK102 (34). A 1 μg aliquot of one of the CPGV cosmid clones is cotransfected along with 1 μg of AcMNPV A4000 viral DNA by the procedure described in Example 1. After 5 days, a standard plaque assay is set up (28). When plaques are fully developed, individual plaques are used to infect single wells of a 48 well tissue culture plate as described in Example 1. Progeny virus from these wells is pooled in groups of 20 and fed to third instar *Trichoplusia ni* larvae in a leaf disk assay as described in Example 2. If a cosmid clone contains a functional analog of p74, it rescues the A4000 virus to oral infectivity. The specific gene responsible for the rescue is identified by repeating the cotransfection and assay protocol with plasmid subclones of the positive cosmid.

BIBLIOGRAPHY

1. Granados, R. R., and Federici, B. A., *The Biology of Baculoviruses*, I, 99 (1986).
2. Tomalski, M. D., and Miller, L. K., *Nature*, 352, 82–85 (1991).
3. Federici, B. A., *In Vitro*, 28, 50A (1992).
4. Martens, J. W. M., et al., *App. & Envir. Microbiology*, 56, 2764–2770 (1990).
5. Menn, J. J., and Borkovec, A. B., *J. Agric. Food Chem.*, 37, 271–278 (1989).
6. Eldridge, R., et al., *Insect Biochem.*, 21, 341–351 (1992).
7. Hammock, B. D., et al., *Nature*, 344, 458–461 (1990).
8. Williamson, M., *Nature*, 353, 394 (1991).
9. Hammock, B., *Nature*, 355, 119 (1992).
10. Luckow, V. A., and Summers, M. D., *Bio/Technoloay*, 6, 47–53 (1988).
11. Miller, L. K., *Ann. Rev. Microbiol.*, 42, 177–199 (1988).
12. Smith, G. E., and Summers, M. D., U.S. Pat. No. 4,745,051.
13. Blissard, G. W., and Rohrmann, G. F., *Ann. Rev. Entomol.*, 35, 127–155 (1990).
14. Partington, S., et al., *Virology*, 175, 91–102 (1990).
15. Kuzio, J., et al., *Virology*, 173, 759–763 (1989).
16. Hill, J. E., et al., *Biochimica et Biophysica Acta*, 1172, 1–2 (1993).
17. Leisy, D. J., et al., *Virology*, 153, 157–167 (1986).
18. Beames, B., and Summers, M. D., *Virology*, 168, 344–353 (1989).
19. Gallo, L. G., et al., *J. Invertebrate Path.*, 58, 203–210 (1991).
20. Crook, N. E., et al., *J. Virology*, 67, 2168–2174 (1993).
21. Passarelli, A. L., and Miller, L. K., *J. Virology*, 67, 2149–2158 (1993).
22. Jarvis, D. L., et al., *Biotechnology*, 8, 950–955 (1990).
23. Presnail, J. K., and Hoy, M. A., *Proc. Natl. Acad. Sci.*, 89, 7732–7736 (1992).
24. Baldarelli, R. M., and Lengyel, J. A., *Nucleic Acids Res.*, 18, 5903–5904 (1991).
25. Zlotkin, E., et al., *Toxicon*, 9, 1–8 (1971).
26. Jackson, J. R. H., and Parks, T. N., U.S. Pat. No. 4,925,664.
27. Sambrook, J., et al., *Molecular Cloning: A Laboratory Manual*, 2nd ed., Cold Spring Harbor Laboratory Press, Cold Spring Harbor, N.Y. (1989).
28. Summers, M. D., and Smith, G. E., *A Manual Of Methods For Baculovirus Vectors And Insect Cell Culture Procedures*, Dept. of Entomology, Texas Agricultural Experiment Station and Texas A & M University, College Station, Tex. 77843–2475, Texas Agricultural Experiment Station Bulletin No. 1555 (1987).
29. Webb, N. R., and Summers, M. D., *Technique*, 2, 173–188 (1990).
30. Roberts, D. B., ed., *Drosophila: A Practical Approach*, page 276, IRL Press, Oxford, England (1986).
31. Luckow, V. A., and Summers, M. D., *Viroloqy*, 170, 31–39 (1989).
32. Johnston, S. A., et al., *Proc. Natl. Acad. Sci.*, 83, 6553–6557 (1986).
33. Fischer, J. A., et al., *Nature*, 332, 853–856 (1988).
34. Knauf, V. C., and Nester, E. W., *Plasmid*, 8, 45–54 (1982).

What is claimed is:

1. A complemented insect virus with reduced capacity for host-to-host transmission in the environment which is rendered noninfectious to insects by alteration of a genetic element of the virus, whose infectivity is restored by complementing with the product or function which is missing from or defective in the altered virus, such that the genetic ability to produce the missing or defective function is substantially absent or completely absent in any of the virus produced from such complementation; wherein such complementation rendering said virus infectious is supplied by a source other than a wild type virus and the virus produced from such complementation is capable of initiating secondary infection that spreads to other insect tissues; wherein the insect virus is a nuclear polyhedrosis virus.

2. The virus of claim 1 wherein the virus is a nuclear polyhedrosis virus selected from the group consisting of *Autographa californica* nuclear polyhedrosis virus, *Heliocoverpa zea* nuclear polyhedrosis virus, *Spodoptera littoralis* NPV, *Heliothis armigera* NPV, *Mamestra brassicae* NPV, and *Rachiplusia ou* NPV.

3. The virus of claim 1 wherein the alteration of a genetic element of the virus is selected from the group consisting of disruption of gene function and interference with viral function.

4. The virus of claim 1 wherein the infectivity of the virus is restored by production of the virus in insect cells transfected with a fragment of DNA which provides the product or function which is missing from or defective in the altered virus.

5. The virus of claim 1 wherein the infectivity of the virus is restored by production of the virus in cell lines which have been stably transformed with a fragment of DNA which provides the product or function which is missing from or defective in the altered virus.

6. The virus of claim 1 wherein the infectivity of the virus is restored by production of the virus in transgenic insects which contain a fragment of DNA which provides the product or function which is missing from or defective in the altered virus.

7. The virus of claim 1 which further comprises a heterologous gene coding for an insect controlling or modifying substance inserted into the viral genome.

8. The virus of claim 2 wherein the virus is *Autographa californica* nuclear polyhedrosis virus.

9. The virus of claim 3 wherein the alteration of a genetic element of the virus is a disruption of gene function selected from the group consisting of a deletion, a frame shift, an insertion, a rearrangement, and a point mutation.

10. The virus of claim 3 wherein the alteration of a genetic element of the virus is an interference with viral function selected from the group consisting of suppression of transcription, suppression of translation, insertion of an additional genetic element, and insertion of an additional regulatory element.

11. The virus of claim 9 wherein the alteration of a genetic element of the virus is a deletion.

12. The virus of claim 11 wherein the alteration of a genetic element of the virus is a deletion in the p74 gene.

13. The virus of claim 12 wherein the virus is *Autographa californica* nuclear polyhedrosis virus.

14. The virus of claim 4 wherein a heterologous promoter is used to control the expression of the fragment of DNA.

15. The virus of claim 4 wherein the virus is a nuclear polyhedrosis virus selected from the group consisting of *Autographa californica* nuclear polyhedrosis virus, *Heliocoverpa zea* nuclear polyhedrosis virus, *Spodoptera littoralis* NPV, *Heliothis armigera* NPV, *Mamestra brassicae* NPV, and *Rachiplusia ou* NPV.

16. The virus of claim 4 wherein the alteration of a genetic element of the virus is selected from the group consisting of disruption of gene function and interference with viral function.

17. The virus of claim 14 wherein the heterologous promoter is selected from the group consisting of viral promoters and cellular promoters.

18. The virus of claim 17 wherein the heterologous promoter is a viral promoter selected from the group consisting of the 6.9K basic protein promoter, the DA26 promoter, the polyhedrin promoter, the 35K promoter, the 39K promoter, the p10 promoter and the IE-1 promoter.

19. The virus of claim 17 wherein the heterologous promoter is a cellular promoter selected from the group consisting of the *Bombyx mori* actin promoter and the *Drosophila melanogaster* hsp 70 promoter.

20. The virus of claim 5 wherein a heterologous promoter is used to control the expression of the fragment of DNA.

21. The virus of claim 20 wherein the heterologous promoter is selected from the group consisting of viral promoters and cellular promoters.

22. The virus of claim 21 wherein the heterologous promoter is a viral promoter selected from the group consisting of the 6.9K basic protein promoter, the DA26 promoter, the polyhedrin promoter, the 35K promoter, the 39K promoter, the p10 promoter and the IE-1 promoter.

23. The virus of claim 21 wherein the heterologous promoter is a cellular promoter selected from the group consisting of the *Bombyx mori* actin promoter and the *Drosophila melanogaster* hsp 70 promoter.

24. The virus of claim 6 wherein a heterologous promoter is used to control the expression of the fragment of DNA.

25. The virus of claim 24 wherein the heterologous promoter is selected from the group consisting of viral promoters and cellular promoters.

26. The virus of claim 25 wherein the heterologous promoter is a viral promoter selected from the group consisting of the 6.9K basic protein promoter, the DA26 promoter, the polyhedrin promoter, the 35K promoter, the 39K promoter, the p10 promoter and the IE-1 promoter.

27. The virus of claim 25 wherein the heterologous promoter is a cellular promoter selected from the group consisting of the *Bombyx mori* actin promoter and the *Drosophila melanogaster* hsp 70 promoter.

28. The virus of claim 7 wherein the insect controlling or modifying substance is selected from the group consisting of toxins, neuropeptides and hormones, and enzymes.

29. The virus of claim 7 wherein the heterologous gene is inserted directly into the site of alteration of the genetic element of the virus.

30. The virus of claim 7 wherein the heterologous gene is inserted adjacent to the site of alteration of the genetic element of the virus, such that segregation of the heterologous gene and the altered genetic element occurs in less than 10% of the viral progeny.

31. The virus of claim 28 wherein the toxin is selected from the group consisting of a toxin from the mite species *Pyemotes tritici*, the toxin AaIT from *Androctonus australis*, a toxin isolated from spider venom, a toxin from *Bacillus thuringiensis* subsp. *aizawai*, and a toxin from *Bacillus thuringiensis* CryIVD.

32. The virus of claim 28 wherein the neuropeptide and hormones are selected from the group consisting of eclosion hormone, prothoracicotropic hormone, adipokinetic hormone, diuretic hormone and proctolin.

33. The virus of claim 28 wherein the enzyme is juvenile hormone esterase.

34. A method for the production of an insect virus with reduced capacity for host-to-host transmission in the environment which comprises the steps of: (1) rendering the virus noninfectious to insects but capable of initiating secondary infection that spreads to other insect tissues by alteration of a genetic element of the virus; and (2) restoring the infectivity of the virus by complementing with the product or function which is missing from or defective in the altered virus, such that the genetic ability to produce the missing or defective function is substantially absent or completely absent in any of the virus produced from such complementation; and wherein such complementation rendering said virus infectious is not supplied by a wild type virus; and the virus is a nuclear polvhedrosis virus.

35. The method of claim 34 wherein the alteration of a genetic element of the virus is selected from the group consisting of disruption of gene function and interference with viral function.

36. The method of claim 34 wherein the alteration of a genetic element of the virus is an interference with viral function selected from the group consisting of suppression of transcription, suppression of translation, insertion of an additional genetic element, and insertion of an additional regulatory element.

37. The method of claim 34 wherein the infectivity of the virus is restored by production of the virus in insect tissue culture cells transfected with a fragment of DNA which provides the product or function which is missing from or defective in the altered virus.

38. The method of claim 34 wherein the infectivity of the virus is restored by production of the virus in insect cell lines which have been stably transformed with a fragment of DNA which provides the product or function which is missing from or defective in the altered virus.

39. The method of claim 34 wherein the infectivity of the virus is restored by production of the virus in transgenic insects which contain a fragment of DNA which provides the product or function which is missing from or defective in the altered virus.

40. The method of claim 34 which further comprises the use of a heterologous promoter.

41. The method of claim 34 which further comprises the use of a heterologous gene coding for an insect controlling or modifying substance inserted into the viral genome.

42. The method of claim 35 wherein the alteration of a genetic element of the virus is a disruption of gene function selected from the group consisting of a deletion, a frame shift, an insertion, a rearrangement, and a point mutation.

43. The method of claim 42 wherein the alteration of a genetic element of the virus is a deletion.

44. The method of claim 43 wherein the alteration of a genetic element of the virus is a deletion in the p74 gene.

45. The virus of claim 15 wherein the virus is *Autographa californica* nuclear polyhedrosis virus.

46. The virus of claim 16 wherein the alteration of a genetic element of the virus is a disruption of gene function selected from the group consisting of a deletion, a frame shift, an insertion, a rearrangement, and a point mutation.

47. The virus of claim 16 wherein the alteration of a genetic element of the virus is an interference with viral function selected from the group consisting of suppression of transcription, suppression of translation, insertion of an additional genetic element, and insertion of an additional regulatory element.

48. The virus of claim 46 wherein the alteration of a genetic element of the virus is a deletion.

49. A complemented insect virus with reduced capacity for host-to-host transmission in the environment which is rendered noninfectious to insects by alteration of a genetic element of the virus, whose infectivity is restored by complementing with the product or function which is missing from or defective in the altered virus, such that the genetic ability to produce the missing or defective function is substantially absent or completely absent in any of the virus produced from such complementation; wherein such complementation rendering said virus infectious is supplied by a source other than a wild type virus and the virus produced from such complementation is capable of initiating secondary infection that spreads to other insect tissues; wherein the virus is a nuclear polyhedrosis virus and wherein the genetic element of the virus is a p74 gene or a p74 homolog of said gene.

50. The virus of claim 49 wherein the virus is a nuclear polyhedrosis virus selected from the group consisting of *Autographa californica* nuclear polyhedrosis virus, *Heliocoverpa zea* nuclear polyhedrosis virus, *Spodoptera littoralis* NPV, *Heliothis armigera* NPV, *Mamestra brassicae* NPV, and *Rachiplusia ou* NPV.

51. The virus of claim 49 wherein the alteration of the p74 gene or gene encoding a p74 homolog is selected from the group consisting of disruption of gene function and interference with viral function.

52. The virus of claim 49 wherein the infectivity of the virus is restored by production of the virus in insect cells transfected with a fragment of the p74 gene or a fragment of gene for a p74 homolog.

53. The virus of claim 49 wherein the infectivity of the virus is restored by production of the virus in cell lines which have been stably transformed with a fragment of the p74 gene or a fragment of gene for a p74 homolog.

54. The virus of claim 49 which further comprises a heterologous gene coding for an insect controlling or modifying substance inserted into the viral genome.

55. The virus of claim 49 wherein the virus is *Autographa californica* nuclear polyhedrosis virus.

56. The virus of claim 49 wherein the virus is *Autographa californica* nuclear polyhedrosis virus.

57. The virus of claim 50 wherein the virus is *Autographa californica* nuclear polyhedrosis virus.

58. The virus of claim 51 wherein the alteration of the p74 gene or gene encoding a p74 homolog is a disruption of gene function selected from the group consisting of a deletion, a frame shift, an insertion, a rearrangement, and a point mutation.

59. The virus of claim 58 wherein the alteration of the p74 gene or gene encoding a p74 homolog is a deletion.

60. The virus of claim 58 wherein the alteration of the p74 gene or gene encoding a p74 homolog is an interference with viral function selected from the group consisting of suppression of transcription, suppression of translation, insertion of an additional genetic element, and insertion of an additional regulatory element.

61. The virus of claim 52 wherein a heterologous promoter is used to control the expression of the fragment of the p74 gene or fragment of a gene encoding a p74 homolog.

62. The virus of claim 52 wherein the alteration of the gene for p74 or for a p74 homolog is selected from the group consisting of disruption of gene function and interference with viral function.

63. The virus of claim 61 wherein the heterologous promoter is selected from the group consisting of viral promoters and cellular promoters.

64. The virus of claim 61 wherein the heterologous promoter is a cellular promoter selected from the group consisting of the *Bombyx mori* actin promoter and the *Drosophila melanogaster* hsp 70 promoter.

65. The virus of claim 63 wherein the heterologous promoter is a viral promoter selected from the group consisting of the 6.9K basic protein promoter, the DA26 promoter, the polyhedrin promoter, the 35K promoter, the 39K promoter, the p10 promoter and the IE-1 promoter.

66. The virus of claim 53 wherein a heterologous promoter is used to control the expression of the fragment of the p74 gene or fragment of a gene encoding a p74 homolog.

67. The virus of claim 66 wherein the heterologous promoter is selected from the group consisting of viral promoters and cellular promoters.

68. The virus of claim 67 wherein the heterologous promoter is a viral promoter selected from the group consisting of the 6.9K basic protein promoter, the DA26 promoter, the polyhedrin promoter, the 35K promoter, the 39K promoter, the p10 promoter and the IE-1 promoter.

69. The virus of claim 67 wherein the heterologous promoter is a cellular promoter selected from the group consisting of the *Bombyx mori* actin promoter and the *Drosophila melanogaster* hsp 70 promoter.

70. The virus of claim 54 wherein the in sect controlling or modifying substance is selected from the group consisting of toxins, neuropeptides and hormones, and enzymes.

71. The virus of claim 54 wherein the heterologous gene is inserted directly into the site of alteration of the genetic element of the virus.

72. The virus of claim 54 wherein the heterologous gene is nserted adjacent to the site of alteration of the genetic element of the virus, such that segregation of the heterologous gene and the altered genetic element occurs in less than 10% of the viral progeny.

73. The virus of claim 70 wherein the toxin is s elected from the group consisting of a toxin from the mite species *Pyemotes tritici*, the toxin AaIT from *Androctonus australis*, a toxin isolated from spider venom, a toxin from *Bacillus thuringiensis* subsp. *aizawai*, and a toxin from *Bacillus thuringiensis* CryIVD.

74. The virus of claim 70 wherein the neuropeptide and hormones are selected from the group consisting of eclosion hormone, prothoracicotropic hormone, adipokinetic hormone, diuretic hormone and proctolin.

75. The virus of claim 70 wherein the enzyme is juvenile hormone esterase.

76. A method for the production of an insect virus with reduced capacity for host-to-host transmission in the environment which comprises the steps of: (1) rendering the virus noninfectious to insects but capable of initiating secondary infection that spreads to other insect tissues by alteration of a genetic element of the virus; and (2) restoring the infectivity of the virus by complementing with the product or function which is missing from or defective in the altered virus, such that the genetic ability to produce the missing or defective function is substantially absent or completely absent in any of the virus produced from such complementation; and wherein such complementation rendering said virus infectious is not supplied by a wild type virus; and the insect virus is a nuclear polyhedrosis virus.

77. The method of claim 76 wherein the alteration of a genetic element of the virus is selected from the group consisting of disruption of gene function and interference with viral function.

78. The method of claim 76 wherein the alteration of a genetic element of the virus is an interference with viral function selected from the group consisting of suppression of transcription, suppression of translation, insertion of an additional genetic element, and insertion of an additional regulatory element.

79. The method of claim 76 wherein the infectivity of the virus is restored by production of the virus in insect tissue culture cells transfected with a fragment of DNA which provides the product or function which is missing from or defective in the altered virus.

80. The method of claim 76 wherein the infectivity of the virus is restored by production of the virus in insect cell lines which have been stably transformed with a fragment of DNA which provides the product or function which is missing from or defective in the altered virus.

81. The method of claim 76 wherein the insect virus comprises a heterologous gene coding for an insect controlling or modifying substance inserted into the viral genome of said insect virus.

82. The method of claim 76 wherein the virus is a nuclear polyhedrosis virus selected from the group consisting of *Autographa californica* nuclear polyhedrosis virus, *Helicoverpa zea* nuclear polyhedrosis virus, *Spodoptera littoralis* NPV, *Heliothis armigera* NPV, *Mamestra brassicae* NPV, and *Rachiplusia ou* NPV.

83. The method of claim 77 wherein the alteration of a genetic element of the virus is a disruption of gene function selected from the group consisting of a deletion, a frame shift, an insertion, a rearrangement, and a point mutation.

84. The method of claim 83 wherein the alteration of a genetic element of the virus is a deletion.

85. The method of claim 81 wherein said heterologus gene coding for an insect controlling or modifying substance is under the control of a heterologous promoter.

86. The virus of claim 55 wherein the alteration of the gene for p74 or for a p74 homolog is a disruption of gene function selected from the group consisting of a deletion, a frame shift, an insertion, a rearrangement, and a point mutation.

87. The virus of claim 55 wherein the alteration of the gene for p74 or for a p74 homolog is an interference with p74 viral function selected from the group consisting of suppression of transcription, suppression of translation, insertion of an additional genetic element, and insertion of an additional regulatory element.

88. The virus of claim 62 wherein the alteration of the gene for p74 or for a p74 homolog is a deletion.

89. The virus of claim 86 wherein the virus is *Autographa californica* nuclear polyhedrosis virus.

* * * * *